US012773141B2

(12) United States Patent
Durr et al.

(10) Patent No.: US 12,773,141 B2
(45) Date of Patent: Oct. 27, 2026

(54) NON-INVASIVE BLOOD ANALYSIS USING A COMPACT CAPILLAROSCOPE AND MACHINE LEARNING TECHNIQUES

(71) Applicant: THE JOHNS HOPKINS UNIVERSITY, Baltimore, MD (US)

(72) Inventors: Nicholas James Durr, Baltimore, MD (US); Gregory N. Mckay, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 540 days.

(21) Appl. No.: 18/257,661

(22) PCT Filed: Dec. 17, 2021

(86) PCT No.: PCT/US2021/064172
§ 371 (c)(1),
(2) Date: Jun. 15, 2023

(87) PCT Pub. No.: WO2022/133296
PCT Pub. Date: Jun. 23, 2022

(65) Prior Publication Data

US 2024/0032827 A1 Feb. 1, 2024

Related U.S. Application Data

(60) Provisional application No. 63/127,668, filed on Dec. 18, 2020.

(51) Int. Cl.
*A61B 5/1455* (2006.01)
*A61B 5/00* (2006.01)
(Continued)

(52) U.S. Cl.
CPC ........ *A61B 5/1455* (2013.01); *A61B 5/14535* (2013.01); *A61B 5/14546* (2013.01);
(Continued)

(58) Field of Classification Search
CPC ... A61B 5/0059; A61B 5/0075; A61B 5/0205; A61B 5/1455; A61B 5/14551;
(Continued)

(56) References Cited

U.S. PATENT DOCUMENTS 7,167,244 B2 1/2007 Mullani
11,244,452 B2 2/2022 Castro-Gonzalez et al.
(Continued)

FOREIGN PATENT DOCUMENTS

CN 104224135 B 1/2017
CN 106580267 A 4/2017
(Continued)

OTHER PUBLICATIONS

Switz et al., "Low-Cost Mobile Phone Microscopy with a Reversed Mobile Phone Camera Lens," PLoS One 9(5), e95330 (2014) (Year: 2014).*
(Continued)

*Primary Examiner* — Chu Chuan Liu
(74) *Attorney, Agent, or Firm* — MH2 Technology Law Group LLP

(57) ABSTRACT

In one example aspect, a system is disclosed that includes an image capture device; a capillaroscope attachable to the image capture device, the capillaroscope including: a light source configured to provide offset light at an angle and location offset from a center horizontal axis and produce oblique remitted light off a patient site; a reverse lens through which the oblique remitted light passes therethrough; and one or more telescopic lenses through which the remitted light passes therethrough to a lens of the image capture device after passing through the reverse lens.

19 Claims, 18 Drawing Sheets

(51) Int. Cl.

| | |
|---|---|
| ***A61B 5/145*** | (2006.01) |
| ***G01N 15/0227*** | (2024.01) |
| ***G01N 33/50*** | (2006.01) |
| ***G01N 33/72*** | (2006.01) |
| ***G06T 7/00*** | (2017.01) |
| ***G06T 15/00*** | (2011.01) |
| *G01N 15/01* | (2024.01) |

(52) U.S. Cl.

CPC ............ *A61B 5/6834* (2013.01); *A61B 5/743* (2013.01); *G01N 15/0227* (2013.01); *G01N 33/5094* (2013.01); *G01N 33/726* (2013.01); *G06T 7/0012* (2013.01); *G06T 15/005* (2013.01); *A61B 2560/02* (2013.01); *A61B 2560/0431* (2013.01); *A61B 2560/0443* (2013.01); *A61B 2560/0462* (2013.01); *A61B 2562/0238* (2013.01); *A61B 2562/146* (2013.01); *A61B 2562/16* (2013.01); *G01N 2015/012* (2024.01); *G01N 2800/22* (2013.01)

(58) Field of Classification Search

CPC ............ A61B 5/14552; A61B 5/14535; A61B 5/14546; A61B 5/6834; A61B 5/6898; A61B 5/7264; A61B 5/743; A61B 2562/0238; A61B 2562/146; A61B 2562/16; G01B 21/0008

See application file for complete search history.

(56) References Cited

U.S. PATENT DOCUMENTS

| | | | | |
|---|---|---|---|---|
| 11,300,774 | B2 | 4/2022 | Dickensheets et al. | |
| 2006/0139640 | A1 | 6/2006 | Mullani | |
| 2008/0086057 | A1* | 4/2008 | Fymat .................. | A61B 5/0059 600/479 |
| 2009/0018414 | A1* | 1/2009 | Toofan ................. | A61B 5/0059 600/473 |
| 2011/0009163 | A1* | 1/2011 | Fletcher ................. | G02B 21/16 455/556.1 |
| 2017/0071516 | A1 | 3/2017 | Bhagat et al. | |
| 2019/0197294 | A1* | 6/2019 | Demirci ............... | G06V 20/693 |
| 2020/0355604 | A1* | 11/2020 | Ntziachristos ..... | G01N 29/2425 |

FOREIGN PATENT DOCUMENTS

| | | | |
|---|---|---|---|
| CN | 107942522 | A | 4/2018 |
| CN | 108024723 | A | 5/2018 |
| CN | 110832378 | A | 2/2020 |
| CN | 111491555 | A | 8/2020 |
| EP | 3716207 | A1 | 9/2020 |
| RU | 2367340 | C2 | 9/2009 |
| UA | 67709 | A | 6/2004 |
| WO | 2015032251 | A1 | 3/2015 |

OTHER PUBLICATIONS

Trachterna, M. (Authorized officer), Extended European Search Report in corresponding European Application No. 21907945.6 mailed on Oct. 21, 2024, 11 pages.

Mckay, Gregory N et al. "Visualization of blood cell contrast in nailfold capillaries with high-speed reverse lens mobile phone microscopy." Biomedical optics express 11.4 (2020): 2268-2276.

Mckay, Gregory N et al. "Imaging human blood cells in vivo with oblique back-illumination capillaroscopy." Biomedical optics express 11.5 (2020): 2373-2382.

Huang, Luojie et al. "A deep learning bidirectional temporal tracking algorithm for automated blood cell counting from non-invasive capillaroscopy videos." Medical Image Computing and Computer Assisted Intervention—MICCAI 2021: 24th International Conference, Strasbourg, France, Sep. 27-Oct. 1, 2021, Proceedings, Part VIII 24. Springer International Publishing, 2021.

Doherty, F. (Authorized officer), International Preliminary Report on Patentability in corresponding International Application No. PCT/US2021/064172 mailed on Jun. 29, 2023, 5 pages.

Kalyamina, I. (Authorized officer), International Search Report and Written Opinion in corresponding International Application No. PCT/US2021/064172 mailed on Apr. 14, 2022, 5 pages.

Chinese Office Action in corresponding Chinese Application No. 202180092994.2 mailed on Nov. 27, 2025, 21 pages, English translation included.

Huang, Luojie, et al. "Automated Blood Cell Counting from Non-invasive Capillaroscopy Videos with Bidirectional Temporal Deep Learning Tracking Algorithm." arXiv (2020): 1-9.

* cited by examiner

182

| CapCyte Non-invasive Blood Analysis | | | |
|---|---|---|---|
| Sex: Female | Age: 35 y.o. | Weight: 60 kg | Height: 170 cm |
| | Not Pregnant | Menstruating | |

Anemia Analysis

| Parameter | Normal Values | Measured | Units |
|---|---|---|---|
| # RBCs | 50 - 500 | 130 | x $10^3$ cells analyzed |
| [RBC] | 4.2 - 5.4 | 3.6 | x $10^6$/μL |
| Hct | 37 - 48 | 39 | % |
| [Hgb] | 12 -15.5 | 12.0 | g/dL |
| MCV | 80 - 100 | 85 | fL |
| **Diagnosis** | | At risk for anemia | |

Sickle Cell Analysis

| Parameter | Normal Values | Measured | Units |
|---|---|---|---|
| # RBCs | 50 - 500 | 130 | x $10^3$ cells analyzed |

NON-INVASIVE BLOOD ANALYSIS USING A COMPACT CAPILLAROSCOPE AND MACHINE LEARNING TECHNIQUES

CROSS-REFERENCE TO RELATED APPLICATIONS

This application is the national stage entry of International Patent Application No. PCT/US2021/064172, filed on Dec. 17, 2021, and published as WO 2022/133296 A1 on Jun. 23, 2022, which claims the benefit of U.S. Provisional Patent Application Ser. No. 63/127,668, filed Dec. 18, 2020, both of which are hereby incorporated by reference herein in their entireties.

BACKGROUND

Blood tests, such as complete blood counts ("CBC") generally require invasive and painful needle blood draws. Repetitive blood draws commonly lead to anemia, patient discomfort, particularly in more sensitive patients (e.g., young children, infants, etc.). Further, protocols limit the frequency at which such tests can be administered. Additionally, blood draws require trained personnel (e.g., a phlebotomist and a lab technician). Expensive laboratory equipment is also required for CBC blood draws and analysis, limiting access in remote and low-resource settings. Yet further, hemolysis of blood cells ex vivo is common as samples age. Still further, blood draws generally require patients to visit a hospital or other care facility.

SUMMARY

In accordance with examples of the present disclosure, a system is disclosed that comprises an image capture device; a capillaroscope attachable to the image capture device, the capillaroscope comprising: a light source configured to provide offset light at an angle and location offset from a center horizontal axis such that the remitted light captured by the capillaroscope has entered the focal plane of the capillaroscope at a net oblique angle; a reverse lens through which the oblique illumination reflection passes therethrough; and one or more telescopic lenses through which the oblique illumination passes therethrough to a lens of the image capture device after passing through the reverse lens.

Various additional features can be included in the system including one or more of the following features. The image capture device is a portable device. The image capture device is a mobile phone. The image capture device is a handheld phone. The capillaroscope further comprises a beam splitter configured to direct light from the light source to provide the offset light. The light source is angled towards the patient site and circumvents the reverse lens. The capillaroscope further comprises one or more beam conditioning components to receive light from the light source or the oblique illumination reflection. The system can further comprise a processor that outputs an operational blood count data as input to a diagnostic workflow to execute the diagnostic workflow based on the oblique illumination reflection that passes through the lens of the image capture device. The diagnostic workflow is executed using a trained neural network. The trained neural network is trained using supervised, unsupervised, or semi-supervised training. The diagnostic workflow includes at least one of: cellular volume determination to determine complete blood count; sickle cell analysis; blood cell concentration determination; hematocrit determination; or hemoglobin concentration determination.

The operational blood count includes at least one of: complete blood count (CBC) data; blood cell masks; viscosity of blood cells; rolling/stickiness of blood cells; blood cell distribution width for sepsis; or temporal trends of blood cell behavior. The system can further comprise a light guide that couples output light from the light source to the patient site and a relay lens system that couples reflected light from the patient site to the reverse lens. The image capture device comprises an application that produces a user interface that shows images captured by the capillaroscope, provides feedback to a user as to a best position of the capillaroscope to acquire accurate measurements, and display results produced by the diagnostic workflow. The image capture device is configured to acquire data in a burst mode to allow short windows of high-speed video to be captured. The system can further comprise a cap that is positioned around the outside of the reverse lens, wherein the cap is disposable or cleanable between uses. The cap provides a suction to stabilize the capillaroscope during use. The image capture device is configured to acquire images at different focal planes during use and produce three-dimensional data that is used by a diagnostic workflow for analyzing 3D cells for diagnosis.

In accordance with examples of the present disclosure, a system is disclosed that comprises a capillaroscope attachable to an image capture device, the capillaroscope comprising: a light source configured to provide offset light at an angle and location offset from a center horizontal axis such that the remitted light captured by the capillaroscope has entered the focal plane of the capillaroscope at a net oblique angle; a reverse lens through which the oblique illumination reflection passes therethrough; one or more telescopic lenses through which the oblique illumination reflection passes therethrough to a lens of the image capture device after passing through the reverse lens; and a processor that outputs an operational blood count data as input to a diagnostic workflow to execute the diagnostic workflow based on the oblique illumination reflection that passes through the lens of the image capture device. The image capture device can comprise an application that produces a user interface that shows images captured by the capillaroscope and display results produced by the diagnostic workflow. The diagnostic workflow includes at least one of: cellular volume determination to determine complete blood count; sickle cell analysis; blood cell concentration determination; hematocrit determination; or hemoglobin concentration determination. The operational blood count includes at least one of: complete blood count (CBC) data; blood cell masks; viscosity of blood cells; rolling/stickiness of blood cells; blood cell distribution width for sepsis; or temporal trends of blood cell behavior.

In accordance with aspects of the present disclosure, a system is disclosed that comprises an image capture device comprising a light source; a light guide that provides light from the light source to a patient site; a capillaroscope attachable to the image capture device, the capillaroscope comprising: a reverse lens through which remitted light from the patient site passes therethrough; and one or more telescopic lenses through which the oblique illumination passes therethrough to a lens of the image capture device after passing through the reverse lens.

In accordance with aspects of the present disclosure, a method is disclosed that comprises directing offset light from a light source at an angle and location offset from a center horizontal axis; receiving remitted light captured by a capillaroscope at a focal plane of the capillaroscope at a net oblique angle; directing the remitted light through a reverse lens; and directing the remitted light that has passed through the reverse lens through one or more telescopic lenses through which the oblique illumination passes therethrough to a lens of an image capture device after passing through the reverse lens.

Various additional features can be included in the method including one or more of the following features. The light source is provided by the image capture device or by another device. The image capture device is a portable device. The image capture device is a mobile phone. The image capture device is a handheld phone. The method further comprises directing the offset set through a beam splitter of the capillaroscope from the light source to provide the offset light. The light source is angled towards the patient site and circumvents the reverse lens. The method further comprises receiving light from the light source or the remitted light by one or more beam conditioning components of the capillaroscope further comprises one or more beam conditioning components to receive light from the light source or the remitted light. The method further comprises processing, by a processor, an operational blood count data as input to a diagnostic workflow to execute the diagnostic workflow based on the remitted light that passes through the lens of the image capture device. The diagnostic workflow is executed using a trained neural network. The trained neural network is trained using supervised, unsupervised, or semi-supervised training. The diagnostic workflow includes at least one of: cellular volume determination to determine complete blood count; sickle cell analysis; blood cell concentration determination; hematocrit determination; or hemoglobin concentration determination. The operational blood count includes at least one of: complete blood count (CBC) data; blood cell masks; viscosity of blood cells; rolling/stickiness of blood cells; blood cell distribution width for sepsis; or temporal trends of blood cell behavior. The method further comprising coupling, by a light guide, output light from the light source to the patient site and a relay lens system that couples reflected light from the patient site to the reverse lens. The method further comprises producing, on the image capture device, an application that produces a user interface that shows images captured by the capillaroscope, provides feedback to a user as to a best position of the capillaroscope to acquire accurate measurements, and display results produced by the diagnostic workflow. The image capture device acquires data in a burst mode to allow short windows of high-speed video to be captured. The method further comprising providing a cap that is positioned around the outside of the reverse lens, wherein the cap is disposable or cleanable between uses. The cap provides a suction to stabilize the capillaroscope during use. The image capture device acquires images at different focal planes during use and produce three-dimensional data that is used by a diagnostic workflow for analyzing 3D cells for diagnosis.

In one example aspect, a system is disclosed comprising an image capture device; a capillaroscope attachable to the image capture device, the capillaroscope comprising: a light source configured to provide offset light at an angle and location offset from a center horizontal axis such that the remitted light captured by the capillaroscope has entered the focal plane of the capillaroscope at a net oblique angle; and one or more telescopic lenses through which the remitted light passes therethrough to a lens of the image capture device after passing through the reverse lens.

Various additional features can be included in the system including one or more of the following features. The image capture device is a portable device. The image capture device is a mobile phone. The image capture device is a handheld phone. The capillaroscope further comprises a beam splitter configured to direct light from the light source to provide the offset light. The light source is angled towards the patient site and circumvents the reverse lens. The capillaroscope further comprises one or more beam conditioning components to receive light from the light source or the oblique remitted light.

In one example aspect, a computer-implemented method is disclosed that includes: training a neural network mapping blood count data to training data; receiving operational input data comprising image data of a patient's capillary; applying the operational input data to the trained neural network; obtaining operational blood count data from the trained neural network; and outputting the operational blood count data as input to a diagnostic workflow to execute the diagnostic workflow.

Various additional features can be included in the system including one or more of the following features. The image data comprises one or more images or videos. The training the neural network comprises training the neural network using supervised, unsupervised, or semi-supervised training. The diagnostic workflow includes at least one of: cellular volume determination to determine complete blood count; sickle cell analysis; blood cell concentration determination; hematocrit determination; or hemoglobin concentration determination. The operational blood count includes at least one of: complete blood count (CBC) data; blood cell masks; viscosity of blood cells; rolling/stickiness of blood cells; blood cell distribution width for sepsis; or temporal trends of blood cell behavior. The operational input data is captured by and received from a dep-operational input data received from a capillaroscope. The capillaroscope is attached to a handheld or portable mobile device or camera device and captures the operational input data as part of a non-invasive medical diagnostic procedure. The operational blood count includes at least one of: complete blood count (CBC) data; blood cell masks; viscosity of blood cells rolling/stickiness of blood cells; blood cell distribution width for sepsis; and temporal trends of blood cell behavior.

In another example aspect, a computer program product includes a computer readable storage medium having program instructions embodied therewith. The program instructions are executable by a computing device to cause the computing device to perform operations including: training a neural network mapping blood count data to training data; receiving operational input data comprising image data of a patient's capillary or other vasculature; applying the operational input data to the trained neural network; obtaining operational blood count data from the trained neural network; and outputting the operational blood count data as input to a diagnostic workflow to execute the diagnostic workflow.

Various additional features can be included in the computer program product including one or more of the following features. The image data comprises one or more images or videos. The training the neural network comprises training the neural network using supervised, unsupervised, or semi-supervised training. The diagnostic workflow includes at least one of: cellular volume determination to determine complete blood count; sickle cell analysis; blood cell concentration determination; hematocrit determination; or hemoglobin concentration determination. The operational blood count includes at least one of: complete blood count (CBC) data; blood cell masks; viscosity of blood cells; rolling/stickiness of blood cells; blood cell distribution width for sepsis; or temporal trends of blood cell behavior. The operational input data is captured by and received from a deep-operational input data received from a capillaroscope. The capillaroscope is attached to a handheld or portable mobile device or camera device and captures the operational input data as part of a non-invasive medical diagnostic procedure. The operational blood count includes at least one of: complete blood count (CBC) data; blood cell masks; viscosity of blood cells rolling/stickiness of blood cells; blood cell distribution width for sepsis; and temporal trends of blood cell behavior.

In another example aspect, a system includes a processor, a computer readable memory, a non-transitory computer readable storage medium associated with a computing device, and program instructions executable by the computing device to cause the computing device to perform operations including: training a neural network mapping blood count data to training data; receiving operational input data comprising image data of a patient's capillary; applying the operational input data to the trained neural network; obtaining operational blood count data from the trained neural network; and outputting the operational blood count data as input to a diagnostic workflow to execute the diagnostic workflow. Various additional features can be included in the system including one or more of the following features. The image data comprises one or more images or videos. The training the neural network comprises training the neural network using supervised, unsupervised, or semi-supervised training. The diagnostic workflow includes at least one of: cellular volume determination to determine complete blood count; sickle cell analysis; blood cell concentration determination; hematocrit determination; or hemoglobin concentration determination. The operational blood count includes at least one of: complete blood count (CBC) data; blood cell masks; viscosity of blood cells; rolling/stickiness of blood cells; blood cell distribution width for sepsis; or temporal trends of blood cell behavior. The operational input data is captured by and received from a deep-operational input data received from a capillaroscope. The capillaroscope is attached to a handheld or portable mobile device or camera device and captures the operational input data as part of a non-invasive medical diagnostic procedure. The operational blood count includes at least one of: complete blood count (CBC) data; blood cell masks; viscosity of blood cells rolling/stickiness of blood cells; blood cell distribution width for sepsis; and temporal trends of blood cell behavior.

DETAILED DESCRIPTION

Figure 1B:
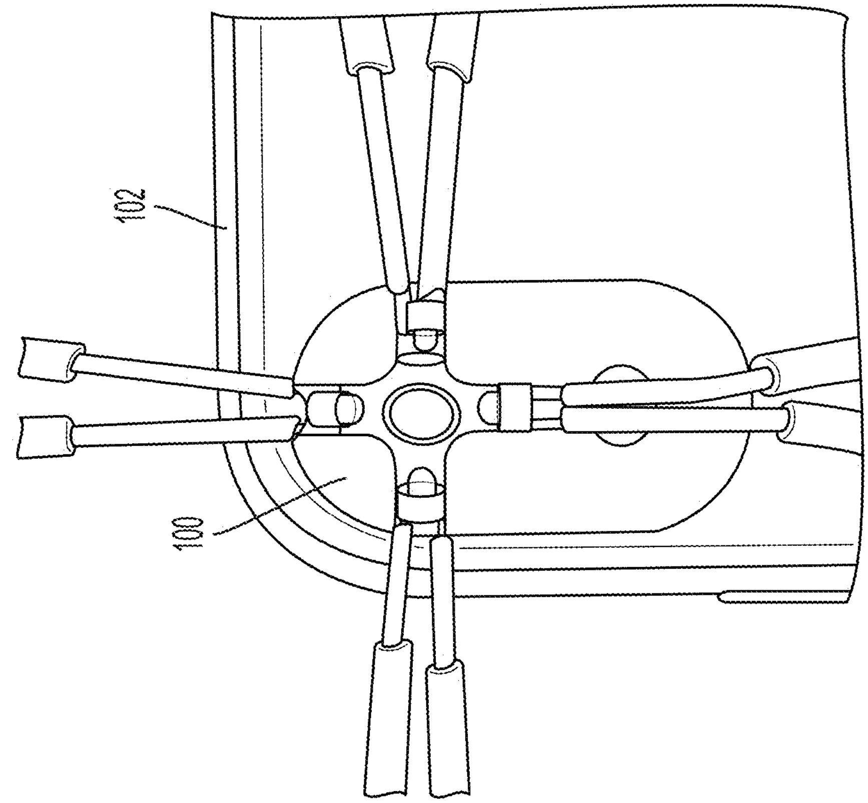
FIG. 1A, FIG. 1B, FIG. 1C, FIG. 1D, FIG. 1E, FIG. 1F, FIG. 1G, FIG. 1H, and FIG. 1I illustrate an overview of an example capillaroscope in accordance with aspects of the present disclosure.

Aspects of the present disclosure may include a system and/or method to conduct accurate non-invasive blood tests, such as complete blood counts ("CBC") using a compact capillaroscope and machine learning techniques. As described herein the compact capillaroscope may be a modular component attachable to a mobile device (e.g., smart phone, tablet, etc.) or other type of portable/handheld camera device. In some embodiments, the capillaroscope may capture images/videos of a testing site on a patient in which capillaries are highly visible. As illustrative examples, the testing site may be a patient's nailfold, within an oral cavity (e.g., on an underside of a patient's bottom lip area, inner lower lip, upper inner lip, ventral tongue, sublingual, conjunctiva, cheek, etc.), or other testing site. It is noted that the techniques described herein are not limited to conducting non-invasive blood tests from a particular testing site. Further, it is noted that the term "images" or "image data" may also refer to "videos" or "video data" and that these terms may be used interchangeably. Also, the term "capillary" may refer to multiple capillaries or larger vessels.

As described herein, the capillaroscope may be configured to provide a phase contrast to image data to improve the detection and visibility of capillaries. In some embodiments, the phase contrast may be provided using a reverse-lens geometry that allows for a wide field-of-view image. Further, an offset illumination source coupled into the field of view in the infinity space or outside of the objective may be provided. In some embodiments, multiple telescope lenses may be provided to increase magnification of the reverse-lens setup. In some embodiments, an offset of illumination and detection axes may produce a gradient of intensity across the field of view, and result in phase contrast due to the net oblique illumination. Some embodiments exploit the detection of differential back and side scattering for blood particle identification. In this way, the capillaroscope, in accordance with aspects of the present disclosure, may produce highly-detailed images and/or videos that may accurately indicate CBC and/or other medical diagnostic information. In some embodiments, the systems and/or methods, described herein, may produce highly-detailed images and/or videos that capture a level of detail of capillaries not possible by current portable and/or handheld camera systems. For example, the systems and/or methods, described herein, may provide absorption contrast and/or other spectral-based information that may distinguish between blood cell types. Additionally, aspects of the present disclosure may provide phase contrast to highlight cellular boundaries including all blood cell types, platelets, and smaller lipid particles. Further, sub-cellular features, such as nuclear envelope and granules, are resolved and can serve as cellular identifiers.

As described herein, the capillaroscope may be relatively inexpensive to fabricate, and does not require extensive training to operate. For example, the capillaroscope, in accordance with aspects of the present disclosure, may be a hand-held device, usable by medical technicians in which the form factor of the capillaroscope may be similar to a thermometer. Thus, non-invasive blood tests may be conducted with relative ease and may be made widely available due to the cost of the systems described herein.

Aspects of the present disclosure may further include a machine learning system that may interpret image data captured by the capillaroscope, described herein, and provide medical diagnostic information based on the image data (e.g., CBC, masks of blood cells, etc.). For example, aspects of the present disclosure may train a neural network by mapping training data (e.g., training image data) with blood count data truths (e.g., CBC truths, mask truths, etc.). In some embodiments, the training data may image data captured by the capillaroscope in which the training data includes the highly-detailed images captured by the capillaroscope. As such, even minor differences between images may be associated with different sets of blood count data truths. In this way, minor differences in the images captured by the capillaroscope may be detected to produce highly accurate estimates of a patient's CBC. In operation, image data of patient's testing site may be captured using the capillaroscope, and this image data may be applied to the trained neural network to estimate the patient's CBC. In some embodiments, the patient's CBC may be output to a diagnostic workflow and used to obtain additional diagnostic information (e.g., red blood cell concentration, hematocrit, hemoglobin concentration, sickle cell analysis, etc.), or for a pre-screening/triage process.

Certain embodiments of the disclosure will hereafter be described with reference to the accompanying drawings, wherein like reference numerals denote like elements. It should be understood, however, that the accompanying drawings illustrate only the various implementations described herein and are not meant to limit the scope of various technologies described herein. The drawings show and describe various embodiments of the current disclosure.

Embodiments of the disclosure may include a system, a method, and/or a computer program product at any possible technical detail level of integration. The computer program product may include a computer readable storage medium (or media) having computer readable program instructions thereon for causing a processor to carry out aspects of the present disclosure.

Figure 1A:
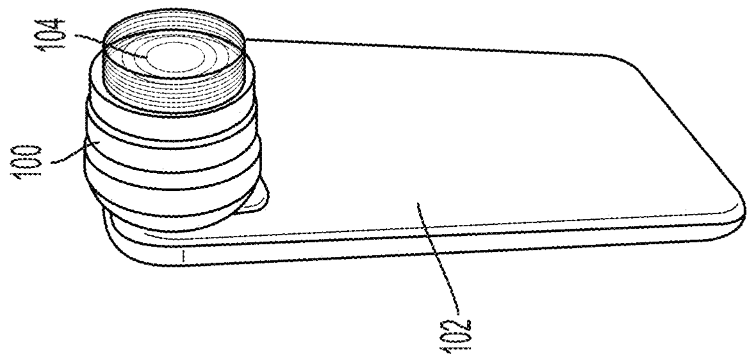

FIG. 1A, FIG. 1B, FIG. 1C, FIG. 1D, FIG. 1E, FIG. 1F, FIG. 1G, FIG. 1H, and FIG. 1I illustrate an overview of an example capillaroscope in accordance with aspects of the present disclosure. As shown in FIG. 1A, a capillaroscope 100 may be attached to a mobile device 102 (e.g., a smart phone, tablet, camera device, etc.). In some embodiments, a sterile cap 104 may be provided (e.g., manufactured from plastic, rubber, and/or a composite material). The sterile cap 104 may be disposable and replaceable between patients. As described in greater herein, the capillaroscope 100 may include a circular extending body to house components to enhance images and videos captured by a camera device of the mobile device 102. In some embodiments, the capillaroscope 100 may include mounting components to mount or attached the capillaroscope 100 to the mobile device 102. Further, the capillaroscope 100 may be detached from the mobile device 102 and attached to a different mobile device 102, detached for storage, or detached when not in use. In an alternative embodiment, and referring to FIG. 1B, the capillaroscope 100 may be flat and placed over the camera device of the capillaroscope 100.

Figure 1C:
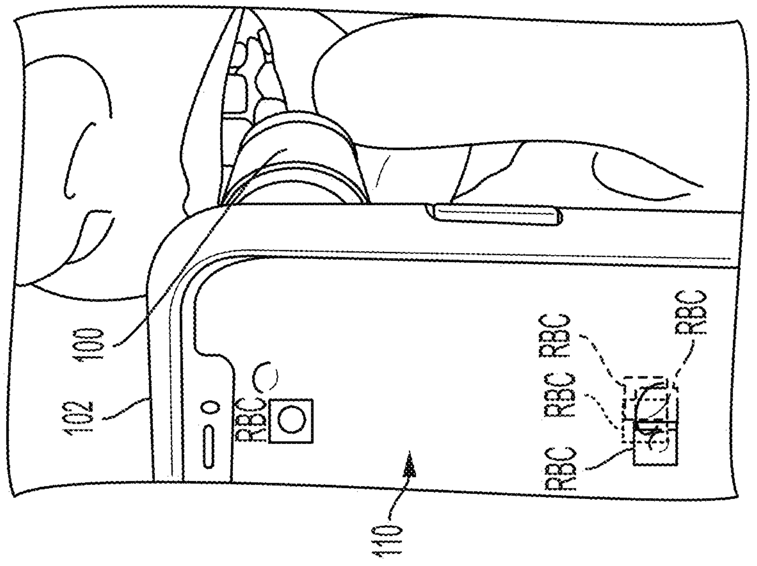
Figure 1D:
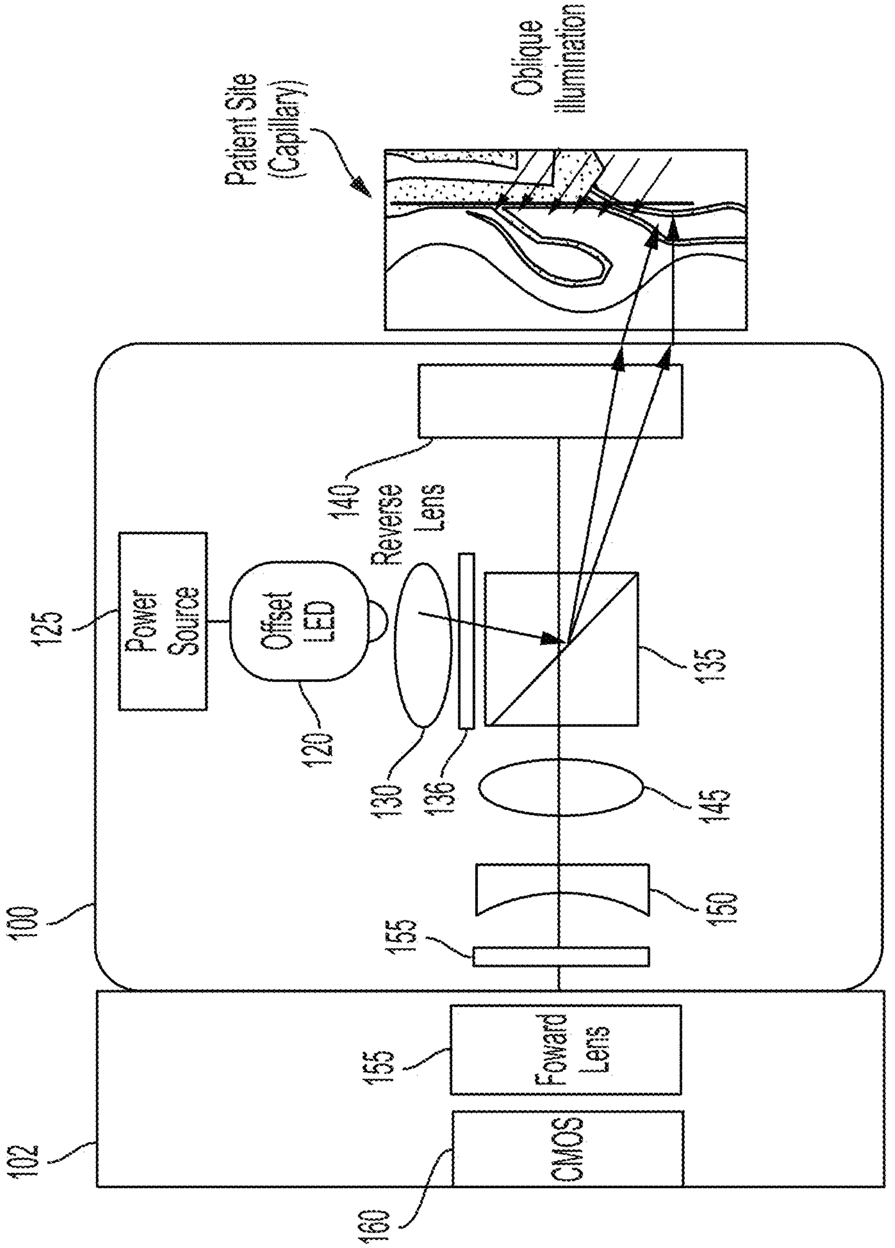

Referring to FIG. 1C, the capillaroscope 100 may be used to capture image data from a patient site, such as from an underside of the patient's lower lip. An example interface 110 is shown in FIG. 1B of the image captured by the capillaroscope 100. In some embodiments, the interface 110 may identify blood cell masks from within the image in which the blood cell masks may be identified using the techniques described in greater detail herein.

As described herein, the capillaroscope 100 may be configured to provide phase contrast and provide an offset illumination source coupled into the field of view in the infinity space or outside of the objective to improve the quality of images/videos of a patient's capillaries captured from a patient testing site using the capillaroscope 100. For example, referring to FIG. 1D, the capillaroscope 100 may include an offset light-emitting diode (LED) 120 powered by a power source 125 (e.g., a battery). As described herein, the offset LED 120 may be configured to provide offset light to the patient site (e.g., at an angle and location offset from a center horizontal axis such that oblique diffuse light is remitted off the patient site, such that the remitted light is captured by the capillaroscope and entered the focal plane of the capillaroscope at a net oblique angle). The offset LED 120 may illuminate light through a condenser lens 130 to converge the light to a beam splitter 135. In some embodiments, the beam splitter 135 may reflect the light from the LED 120 towards the patient site in a manner such that the light is offset at the patient site (e.g., to create a phase offset when the diffuse light is detected off of the patient site). For example, As further shown in FIG. 1D, oblique diffuse illumination of the patient site (e.g., the patient's capillaries) may be generated as a result of the offset light. In some embodiments, the beam splitter 135 may be configured to direct the light at an angle such that the light remitted by the patient's capillaries in a manner that form the oblique diffuse light, as shown. As described herein, the oblique diffuse light that has been remitted by the patient's capillaries may generate a phase contrast, which improves the detection and illumination of features in images and videos of the patient's capillaries.

In some embodiments, the oblique diffuse light remitted back from the patient's capillaries may pass through the reverse lens 140, and through a first telescopic lens 145 and a second telescopic lens 150. The first telescopic lens 145 and the second telescopic lens 150 may magnify the remitted light (e.g., by a factor of two) and the magnified light may be received by the mobile device 102. More specifically, the remitted light may be received by a forward lens and a processed by an image processor (e.g., a CMOS 160) of the mobile device 102 (e.g., when image data is captured by the mobile device 102, such as during a medical testing process in which the mobile device 102 along with the capillaroscope 100 are used to capture images and videos of the patient's capillary).

In some embodiments, the capillaroscope 100 may include additional components to condition light from the offset LED 120 and the light remitted back from the patient's site. For example, the capillaroscope 100 may include beam conditioners 136 and 155, which may include as polarizers and/or wavelength filters, grid patterns for obtaining phase contrast and/or optical sectioning, aberration correction components to improve off-axis resolutions, multi-wavelength components to allow for spectroscopy, etc. In some embodiments, the first telescopic lens 145 and/or the second telescopic lens 150 may include one or more aberration corrective elements, such as a lithography mask. By capturing image data using the capillaroscope 100, a phase contrast is introduced in which the phase contrast more clearly and visually differentiates between features in the capillaries, such as blood cell mask boundaries and/or other features that may be analyzed for blood test analysis based on visual image/video data captured by the mobile device 102 using the capillaroscope 100.

In some embodiments, the offset LED 120 may be angled and arranged so as to circumvent the reverse lens 140. For example, referring to FIG. 1E, the offset LED 120 may be angled towards the patient site and circumvent the reverse lens 140 to create oblique illumination without the need for the beam splitter 135. By omitting the reverse lens 140, the physical size of the capillaroscope 100 may be reduced.

Figure 1E:
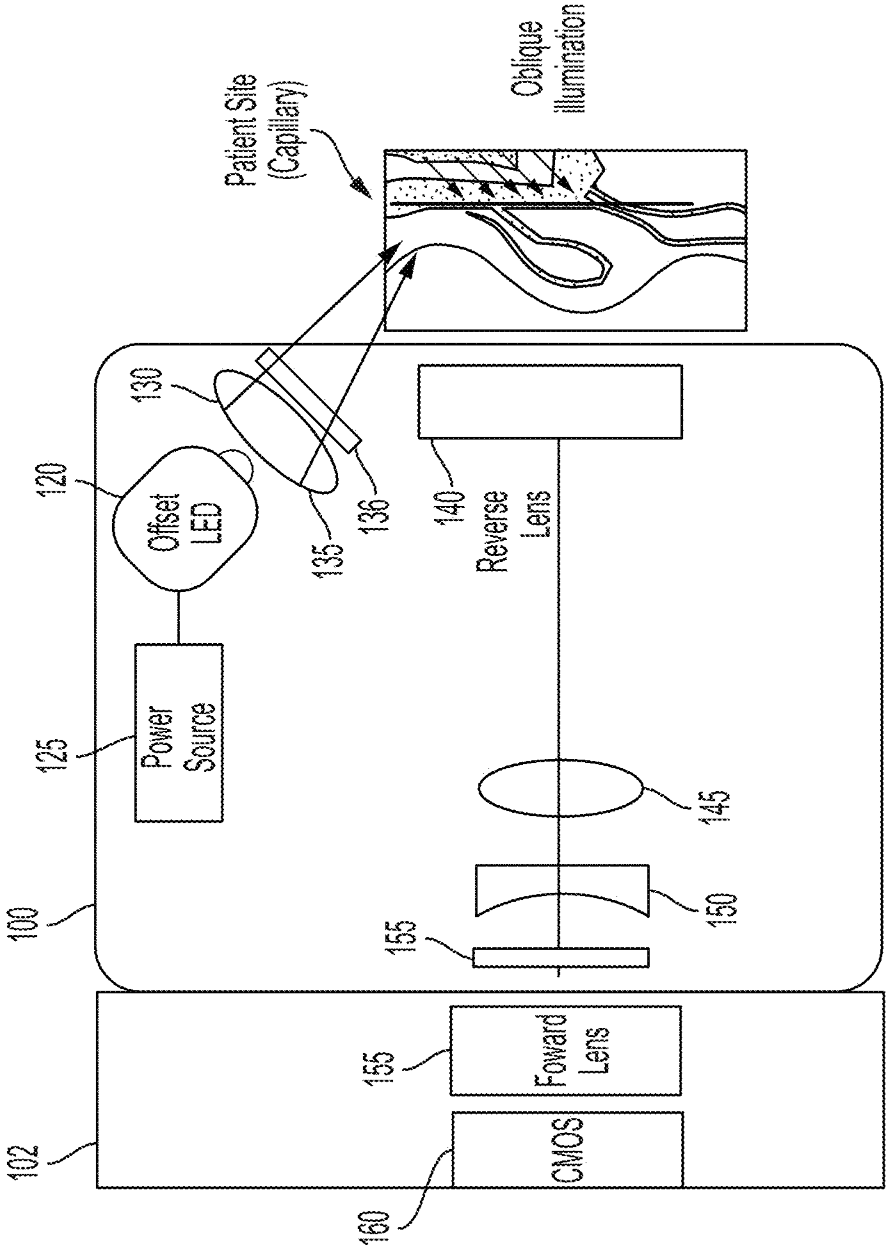
Figure 1F:
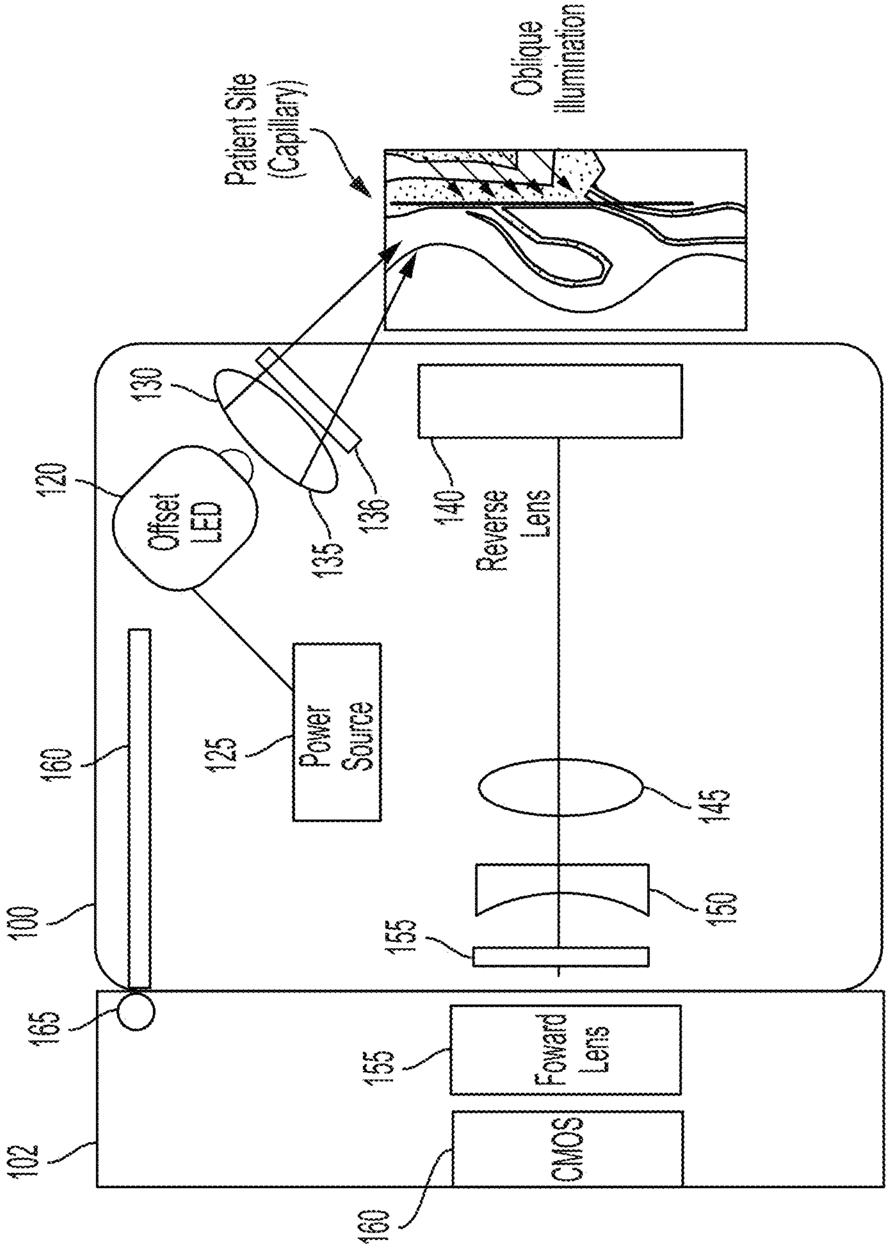

In some embodiments, and referring to FIG. 1F, the capillaroscope 100 may include a light pipe 160 (e.g., a fiber optic component, prisms, reflecting tube, or the like) to direct light from a flash 165 integrated natively in the mobile device 102 towards the patient site. Advantageously, the illumination from the flash 165 may be synched with the acquisition and also. Further the light pipe 160 in conjunction with the flash 165 may provide relatively bright, short-duration illumination to avoid motion noise and further enhance contrast.

Figure 1G:
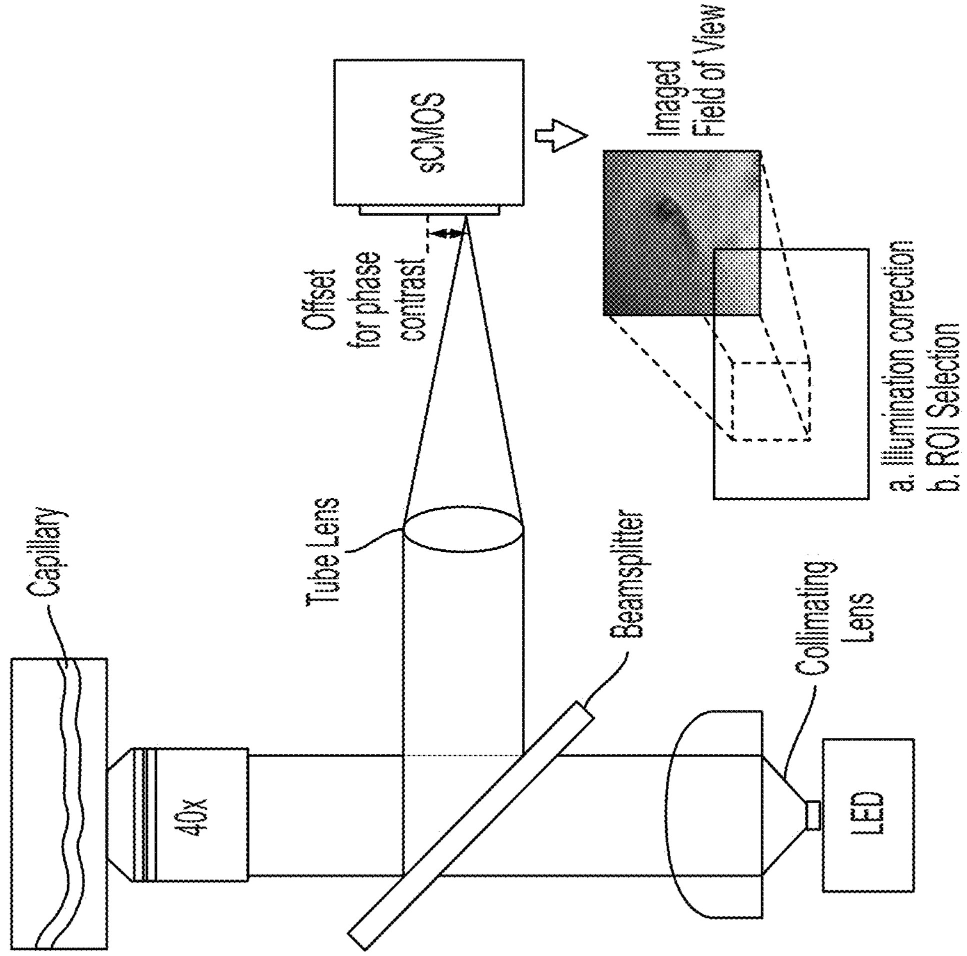

FIG. 1G shows the capillaroscope 100 that includes a LED 170, a collimating lens 172, a beamsplitter 174, a focusing element 176 that focuses light from a first path produced by the beamsplitter 174 to capillary area 178, a tube lens 180 that receives light from a second path from the beamsplitter 174 to detector 176.

Figure 1H:
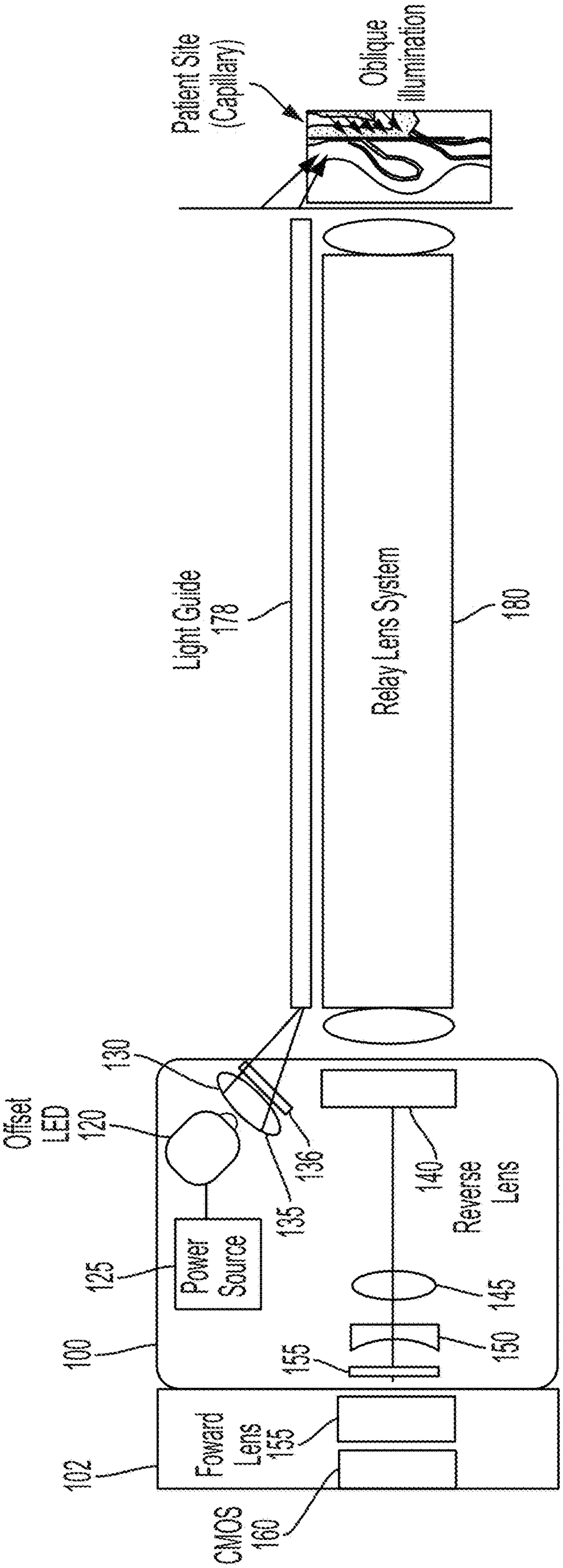

FIG. 1H shows the capillaroscope 100 of FIG. 1E with the addition of a light guide 178 that couples light from offset LED 120 to the patient site and a relay lens system 180 that conveys remitted light from the patient site to the reverse lens 140.

Figure 1I:
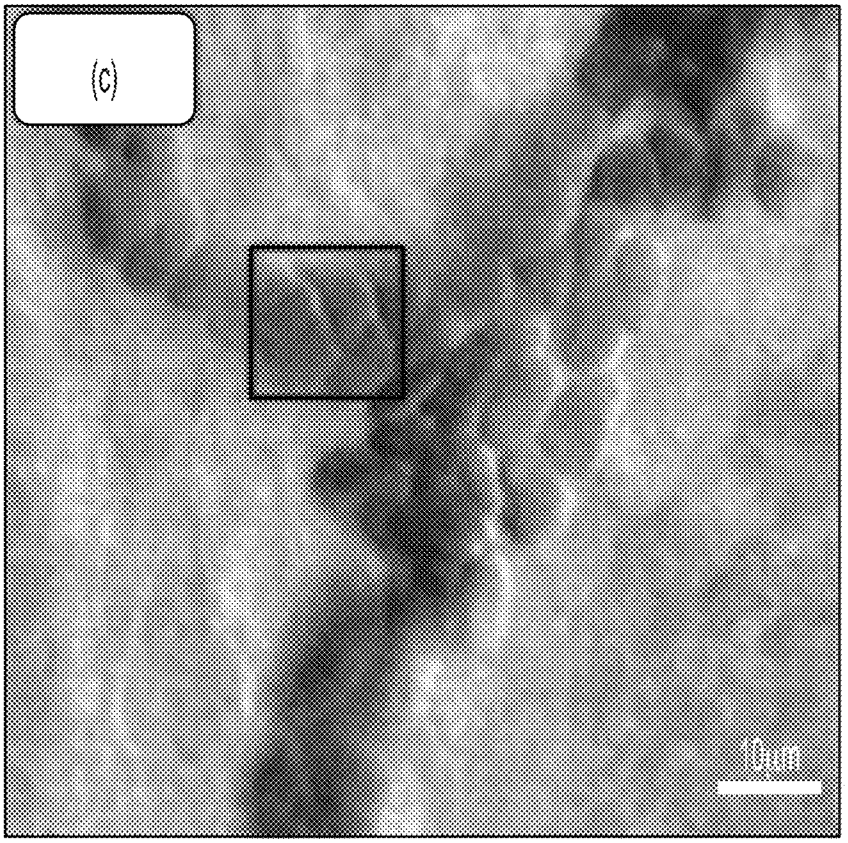
Figure 11:
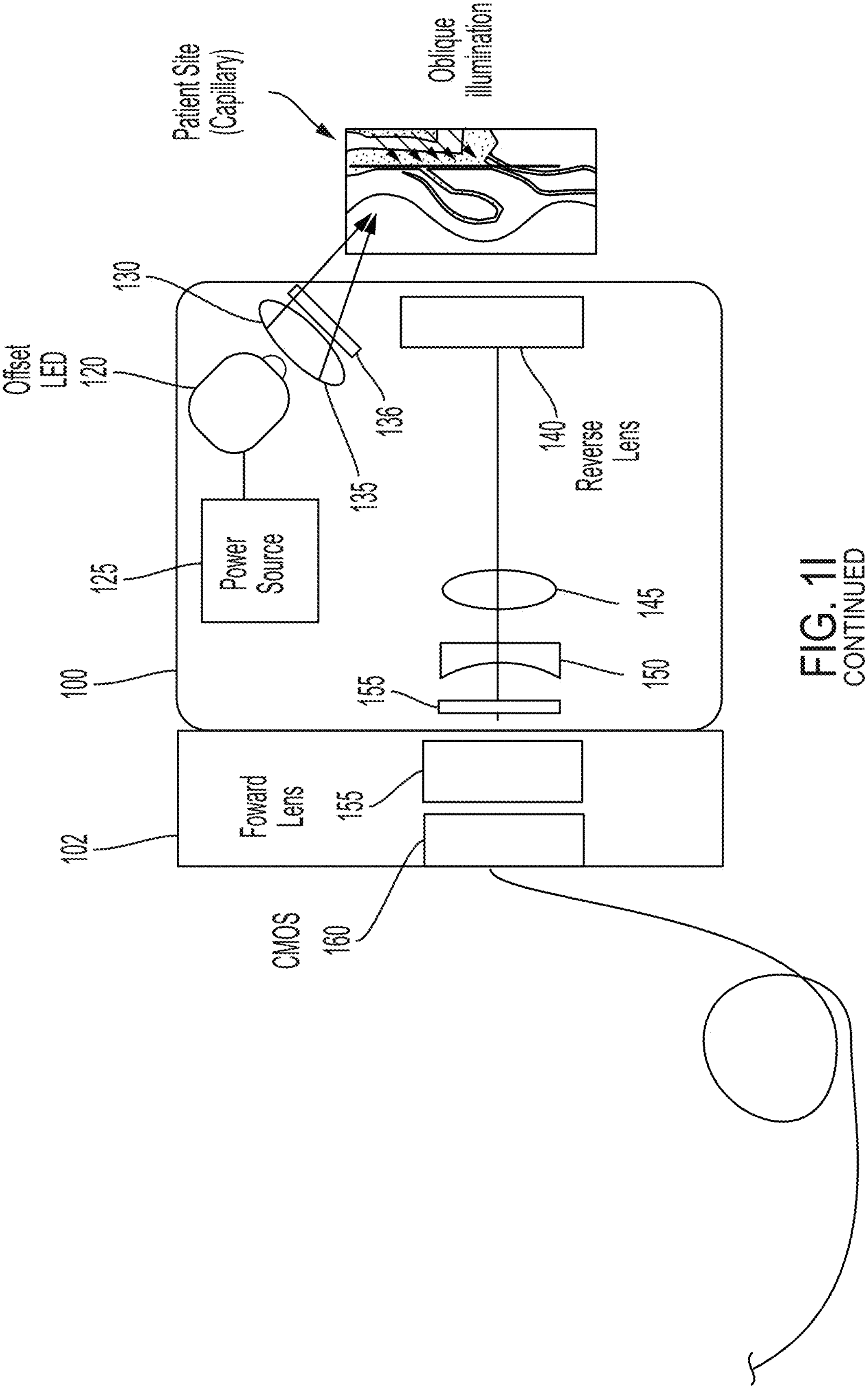

FIG. 1I shows the capillaroscope 100 of FIG. 1E with the addition of a smart phone application 182 that displays images acquired by the capillaroscope 100 and the results produced as a result of the processing in a user interface. This figure shows a configuration where the camera, lens, and light source are on a "remote head" that acquires data and sends it to a smart phone wirelessly or through a cable attachment for display and analysis. Like a smart thermometer that you would put under your tongue and it plugs into a smart phone.

In some examples, the capillaroscope 100 can include a includes a suction mechanism on the cap to stabilize the field. In some examples, the mobile device 102 can include a user-interface will guide the operator to position the capillaroscope 100 in a suitable position to record high-quality capillary videos. In some examples, the mobile device 102 can include a user-interface will automatically analyze the videos and also take prior knowledge as input (age, weight, ethnicity, gender, pregnancy, etc.) and output diagnostic values similar to CBC. In some examples, the capillaroscope 100 or the mobile device 102 can also measure heart rate, temperature, other combined sensors incorporating that data into measurement. In some examples, the mobile device 102 can include one or more algorithms to autofocus onto capillary. In some examples, the capillaroscope 100 or the mobile device 102 can also complete axial sweeps quickly change z-focus to get 3D information about specific cells. In some examples, capillaroscope 100 can be configured to measure blood velocity and blood vessel size.

Figure 2:
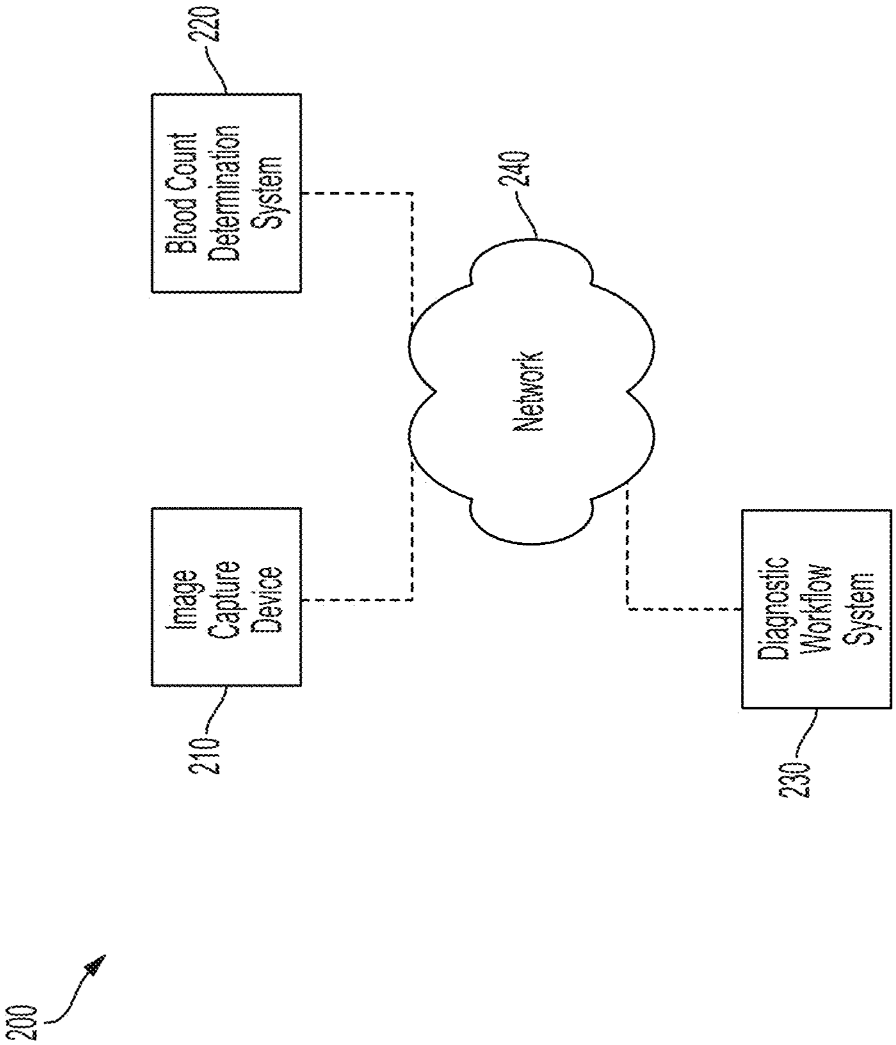
FIG. 2 illustrates an example environment for conducting non-invasive blood tests in accordance with aspects of the present disclosure.

FIG. 2 illustrates an example environment for conducting non-invasive blood tests in accordance with aspects of the present disclosure. As shown in FIG. 2, environment 200 includes an image capture device 210, a blood count determination system 220, a diagnostic workflow system 230, and a network 240.

The image capture device 210 may include a computing device and/or camera device capable of communicating via a network, such as the network 240. In example embodiments, the image capture device 210 may include mobile communication device (e.g., a smart phone or a personal digital assistant (PDA)), a tablet device, or the like. In some embodiments, the image capture device 210 may include the capillaroscope 100 with the mobile device 102 attached, however, the image capture device 210 may include any other type of camera or image capture device. In some embodiments, the image capture device 210 may be hand-held device used to capture image data of a patient's site as part of a non-invasive medical testing procedure (e.g., a blood count testing procedure, as described herein). That is, the image capture device 210 may function as a hand-held non-invasive testing device.

The blood count determination system 220 may include one or more computing devices that determines blood count information based on image data received from the image capture device 210. In some embodiments, the blood count determination system 220 may build, update, and/or maintain a machine learning system (e.g., a neural network) used to interpret image data (e.g., of a patient's capillary). More specifically, the blood count determination system 220 may receive image data, apply the image data to the neural network, and obtain, from the neural network, blood count information (e.g., CBC values, information identifying blood cell mask boundaries/locations in the image data, etc.). In some embodiments, the blood count determination system 220 may output the blood count information to the diagnostic workflow system 230. In this way, blood count information may be determined from image data obtained from the image capture device 210 via a non-invasive medical procedure.

The diagnostic workflow system 230 may include one or more computing devices that receives the blood count information (e.g., from the blood count determination system 220). In some embodiments, the diagnostic workflow system 230 may use the blood count information to execute any variety of diagnostic workflows. For example, the diagnostic workflow system 230 may use the blood count information to perform sickle cell analysis (e.g., by applying the blood count information to neural network that predicts sickle cell analysis from the blood count information). Additionally, or alternatively, the diagnostic workflow system 230 may determine blood cell concentration from the blood count information. Additionally, or alternatively, the diagnostic workflow system 230 may determine at least one of: cellular volume determination to determine complete blood count; sickle cell analysis; blood cell concentration determination; hematocrit determination; or hemoglobin concentration determination. The operational blood count includes at least one of: complete blood count (CBC) data; blood cell masks; viscosity of blood cells; rolling/stickiness of blood cells; blood cell distribution width for sepsis; or temporal trends of blood cell behavior. Additionally, or alternatively, the diagnostic workflow system 230 may be used to perform some other diagnostic function based on the blood count information.

The network 240 may include network nodes and one or more wired and/or wireless networks. For example, the network 240 may include a cellular network (e.g., a second generation (2G) network, a third generation (3G) network, a fourth generation (4G) network, a fifth generation (5G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network 240 may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks. In embodiments, the network 240 may include copper transmission cables, optical transmission fibers, wireless transmission, routers, firewalls, switches, gateway computers and/or edge servers.

The quantity of devices and/or networks in the environment 200 is not limited to what is shown in FIG. 2. In practice, the environment 200 may include additional devices and/or networks; fewer devices and/or networks; different devices and/or networks; or differently arranged devices and/or networks than illustrated in FIG. 2. Also, in some implementations, one or more of the devices of the environment 200 may perform one or more functions described as being performed by another one or more of the devices of the environment 200. For example, the image capture device 210 may perform functions described as being performed by the blood count determination system 220. That is, the image capture device 210 may include a software component that locally performs the functions the blood count determination system 220 without involving the network 240. Devices of the environment 200 may interconnect via wired connections, wireless connections, or a combination of wired and wireless connections.

Figure 3:
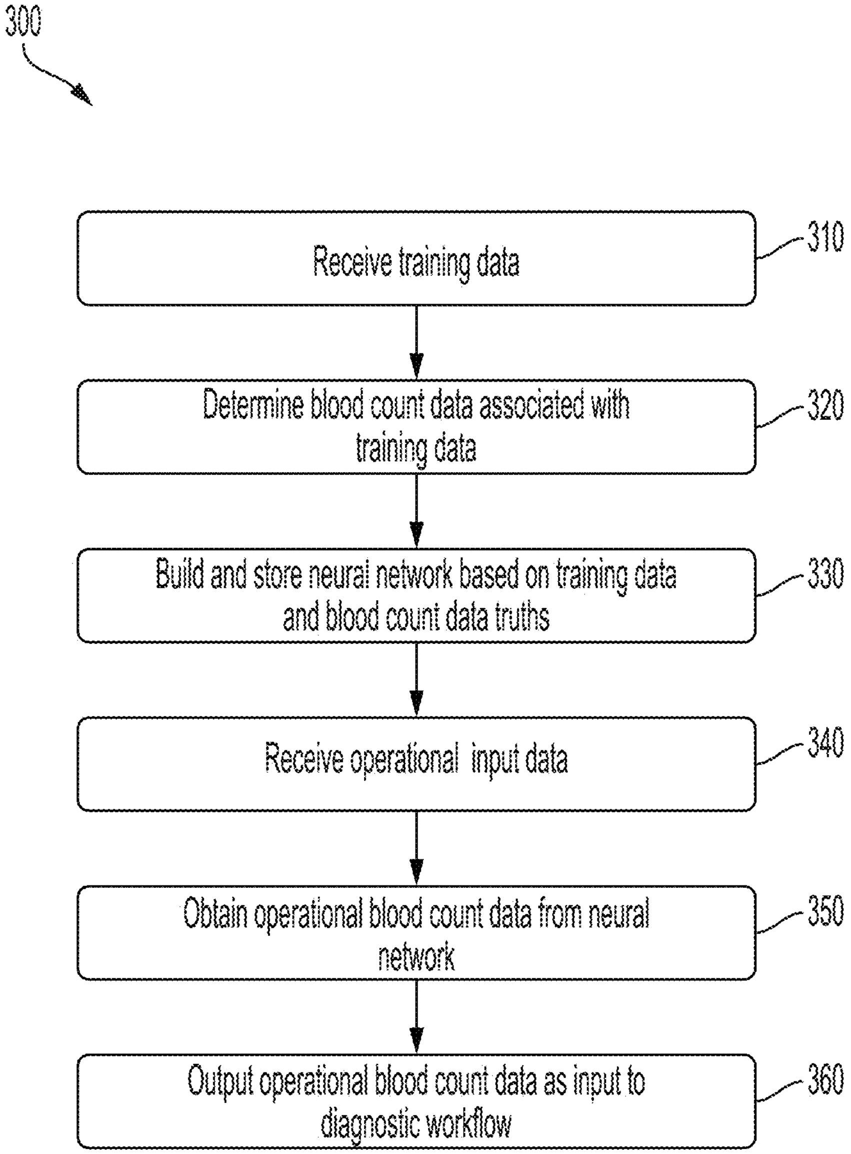
FIG. 3 illustrates an example flowchart of a process for training and using a machine learning system to determine blood count information from image data obtained by a non-invasive testing device.

FIG. 3 illustrates an example flowchart of a process for training and using a machine learning system to determine blood count information from image data obtained by a non-invasive testing device. The blocks of FIG. 3 may be implemented in the environment of FIG. 2, for example, and are described using reference numbers of elements depicted in FIG. 2. As noted herein, the flowchart illustrates the architecture, functionality, and operation of possible implementations of systems, methods, and computer program products according to various embodiments of the present disclosure.

As shown in FIG. 3, The process 300 may include receiving training data mapping image data to blood count data truths (block 310). For example, the blood count determination system 220 may receive training data (e.g., training image data) captured by a non-invasive testing device (e.g., image capture device 210). In some embodiments, multiple sets of training image data may be received as part of a training process The process 300 may also include determining blood count data associated with the training data (block 320). More specifically, the blood count determination system 220 may determine the blood count data linked to the training data (e.g., red blood cell counts by volume, white blood cell counts by volume, granulocyte counts, monocyte counts, lymphocyte counts, granulocyte classification (neutrophils vs eosinophils vs basophils) platelet counts, etc. Other blood count data may include biomarkers, such as mean cellular volume, viscosity, rolling/stickiness of cells, blood cell distribution width for infection and sepsis (RDW, monocytes), and/or temporal trends of such biomarkers and blood cell behaviors (e.g., minute-to-minute Neutrophil counts, such as for neonates). In some embodiments, the blood count data may include masks of red blood cells.

In some embodiments, unsupervised deep learning techniques may be used to determine the blood count data linked to the training data. As one example, the training data may include video data in which deep learning may be applied to track objects frame-by-frame in the video data. The deep learning techniques, described herein, may track objects in the video data to detect, classify, and/or count the different blood cell constituents. In some embodiments, any suitable deep learning framework and/or techniques may be used to segment and count blood cells from training video inputs (e.g., clustering, association, etc.). While generally, unsupervised deep learning techniques may be used to determine the blood count data truths, supervised and/or semi-supervised machine learning techniques may be used in which previously known blood count data truths/labels may be linked to the training data.

The process 300 also may include building and storing a neural network based on the training data (block 330). For example, the blood count determination system 220 may build the neural network as additional training data is received. In some embodiments, the determined blood count data (e.g., determined at block 320) may be linked to corresponding sets of training input data (e.g., received at block 310). Further, the neural network may be refined and improved using back propagation, supervised/semi-supervised confirmation input, and/or other neural network refinement techniques. In some embodiments, other machine learning systems may be trained in addition to, or instead of, a neural network.

The process 300 further may include receiving operational input data (block 340). For example, the blood count determination system 220 may receive operational input data including image data captured by the image capture device 210 of a patient's site in which blood count information is unknown. More specifically, a medical professional may use the image capture device 210 to capture image data of the patient's site as part of a non-invasive medical procedure to obtain the patient's blood count information. As described herein, the operational input data may include highly-detailed images with a phase contrast of the patient's capillaries.

The process 300 also may include obtaining blood count data from the neural network (block 350). For example, the blood count determination system 220 may apply the operational input data to the neural network (e.g., built and stored at block 330) to obtain blood count data from the operational input data. As described herein, since the operational input data includes highly-detailed images with a phase contrast of the patient's capillaries, and since the neural network is trained based on highly-detailed training images, the blood count determination system 220 may obtain, from the neural network, accurate blood count information. In other words, slight discrepancies between different operational input images may result in the neural network returning different blood count data. As described herein, the blood count data may include a complete blood count (CBC), information defining one or more masks of one or more red blood cells, and/or other information related to blood count.

The process 300 further may include outputting blood count data as input to a diagnostic workflow (block 360). For example, the blood count determination system 220 may output the blood count data to the diagnostic workflow system 230. Based on receiving the blood count data, the diagnostic workflow system 230 may execute any variety of diagnostic workflows that use the blood count data as input.

Figure 4:
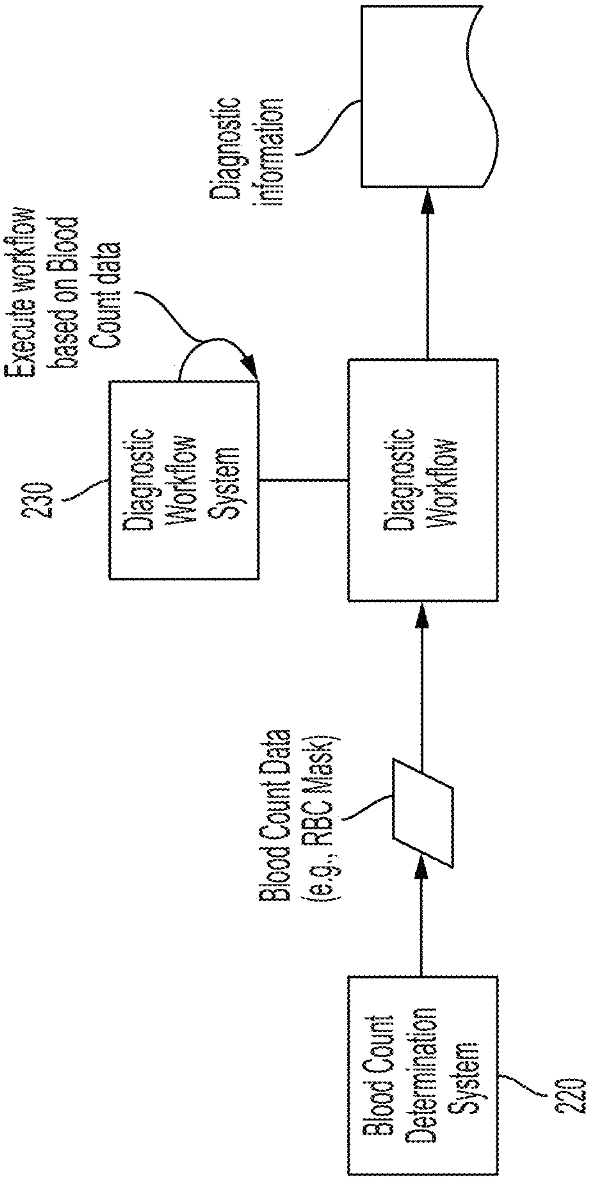
FIG. 4 illustrates an example diagram for executing a diagnostic workflow based on blood count information obtained using a non-invasive testing device as described herein.

Referring to FIG. 4, the blood count determination system 220 may output the blood count data (e.g., an RBC mask) to the diagnostic workflow system 230. The diagnostic workflow system 230 may execute a diagnostic workflow based on the blood count data. As one example, the diagnostic workflow system 230 may perform sickle cell analysis by applying the blood count data to a neural network configured to perform sickle cell analysis based on the blood count data. Additionally, or alternatively, the diagnostic workflow system 230 may determine an RBC concentration based on the blood count data. Additionally, or alternatively, the diagnostic workflow system 230 may determine a hematocrit and/or a hemoglobin concentration based on the blood count data. Additionally, or alternatively, the diagnostic workflow system 230 may perform at least one of: cellular volume determination to determine complete blood count; sickle cell analysis; blood cell concentration determination; hematocrit determination; or hemoglobin concentration determination. The operational blood count includes at least one of: complete blood count (CBC) data; blood cell masks; viscosity of blood cells; rolling/stickiness of blood cells; blood cell distribution width for sepsis; or temporal trends of blood cell behavior. Additionally, or alternatively, the diagnostic workflow system 230 may perform another type of diagnostic test based on the blood count data, such as age, pregnancy status, height/weight, etc.

Based on performing the diagnostic workflow, the diagnostic workflow system 230 may output diagnostic information. In some embodiments, the diagnostic information may be used by a medical professional to treat a patient accordingly (e.g., arrange for follow-up tests, provide medical consulting, prescribe medication, schedule a procedure, and/or perform any other treatment as appropriate).

The task of OBC cell tracking is unique and challenging. Cells of a given class have similar appearances, with similar sizes, shapes, and granularity. Moreover, the shapes of individual cells tend to change from rotation and collision as they flow through crowded capillaries. Therefore, it is difficult to distinguish and track individual cells using appearance-based MOT models. To solve the above challenges, another kind of tracker is used that achieves object association based on position and movement information. For example, SORT, a predictive tracking model, tracks in a forward manner, assuming that objects move in a predictable and continuous pattern over time and space; CenterTrack, a tracking-by-detection model, works in a retrospective way by globally matching a constellation of current object centers backward to the previous frame. In OBC videos, blood cells move in fixed directions along capillaries, which approximately meets the SORT assumption. Blood cell tracking is also an appropriate use case for CenterTrack as relative positions among nearby cells in crowded capillaries tend to remain consistent throughout flow. Another benefit of combining SORT and CenterTrack is that SORT maintains a long-term memory of flow velocity by continuously recording the flow history, whereas CenterTrack allows for short-term changes in velocity while enforcing similar relative positions of detected cells. Following these intuitions, an architecture, called CycleTrack, is used by combining SORT and CenterTrack into a robust tracker that tracks objects in both temporal directions. Moreover, such position-based trackers are able to perform higher-speed blood cell analysis which is significant for point-of-care application.

Figure 5:
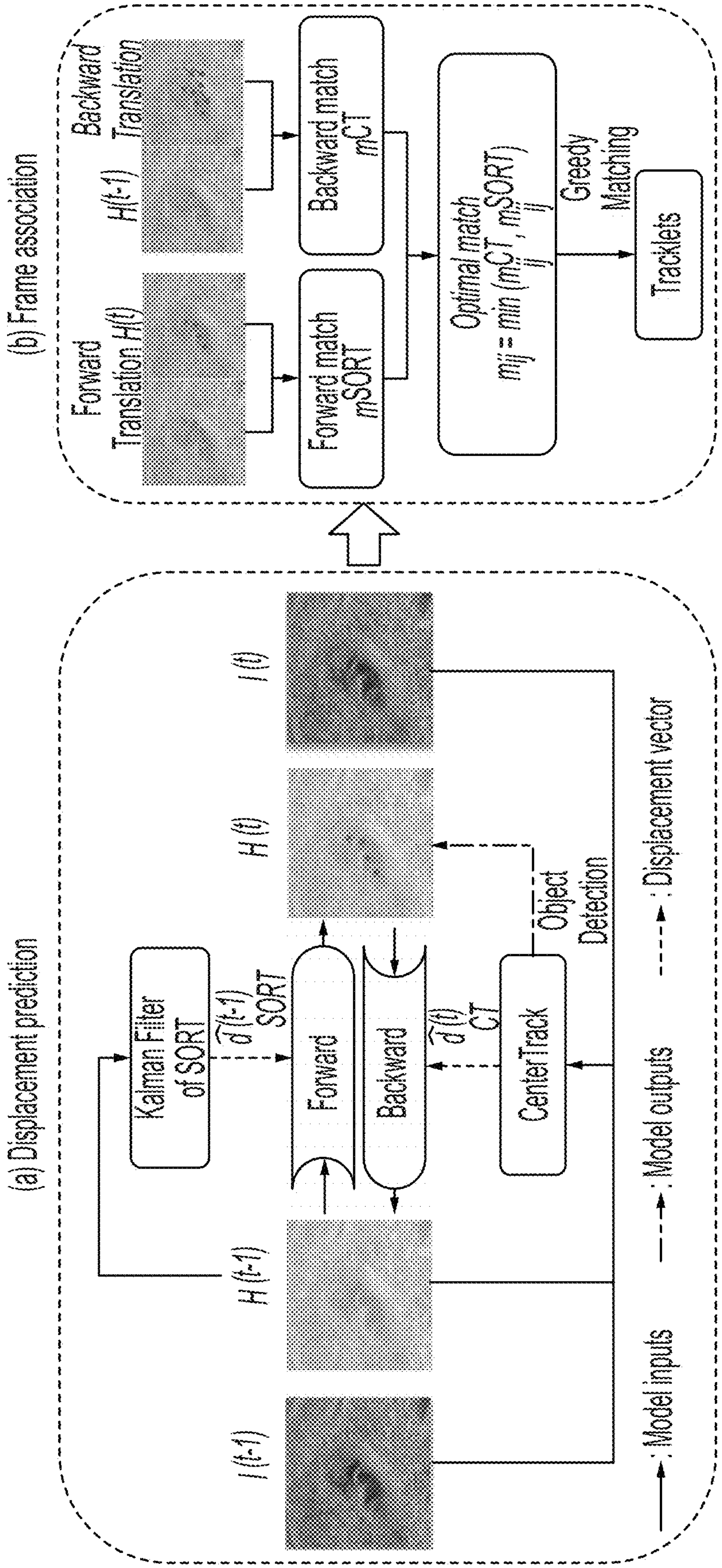
FIG. 5 shows a workflow of CycleTrack Framework where $H^{(t)} \in \mathbb{R}^{W \times H \times 1}$ represents the center heatmap of detected cells at time t according to examples of the present disclosure.

FIG. 5 shows a workflow of CycleTrack Framework where $H^{(t)} \in \mathbb{R}^{W \times H \times 1}$ represents the center heatmap of detected cells at time t according to examples of the present disclosure.

The CycleTrack framework is shown in FIG. 5. CycleTrack combines Center-Track and SORT to achieve backward and forward tracking between two consecutive frames. In this section, the description of CycleTrack is organized around its three key components of CenterTrack, SORT, and association of new cell detections with previously existing cell tracks, termed as tracklets.

CenterTrack is a single deep network that solves object detection and tracking jointly and is trained end-to-end. CenterTrack uses a CenterNet detector, which takes a single image as the input and outputs object detections. Each detection y=(p, s, c, id) is represented by its center location ($p \in \mathbb{R}^2$), size of the bounding box ($s \in \mathbb{R}^2$), a confidence score ($c \in [0,1]$) and a detection id ($id \in \mathbb{R}^+$). The architecture of CenterTrack is nearly identical to CenterNet, simply expanding the input and output channels to achieve multiple tasks. CenterTrack takes two consecutive frames: $I^{(t)} \in \mathbb{R}^{W \times H \times 1}$ and $I^{(t-1)} \in \mathbb{R}^{W \times H \times 1}$, and the prior tracked objects $$O^{(t-1)} = \{y_0^{(t-1)}, y_1^{(t-1)}, \ldots\}$$

as inputs, and outputs current object detections with an additional 2D displacement map $\widetilde{D}^{(t)} \in \mathbb{R}^{W \times H \times 2}$, where W and H represent the width and height of input frames. A displacement vector $\widetilde{d}^{(t)}$ for each object could then be extracted from $\widetilde{D}^{(t)}$.

To restrict displacement estimations to adhere to the assumption that all blood cells in the same frame should move in similar directions, a base vector $$\vec{d}_{base}^{(t-1)}$$

is introduced, which is the average displacement vector of all cells from frame (t−1). This base vector is used to refine displacement vector predictions from CenterTrack, $$\widetilde{d}_{CT_i}^{(t)}:$$

$$\widetilde{d}_{CT_i}^{(t)} = w_i \widetilde{d}_i^{(t)} + |1 - w_i| \widetilde{d}_{base}^{(t-1)} \tag{1}$$

$$\text{where } w_i = \frac{\widetilde{d}_{base}^{(t-1)} \cdot \widetilde{d}_i^{(t)}}{|\widetilde{d}_{basw}^{(t-1)}||\widetilde{d}_i^{(t)}|}.$$

This equation provides a weighted, corrective action on the conventional displacement vector prediction from CenterTrack. The more $\vec{d}^{(t)}$ deviates from $$\vec{d}^{(t-1)}_{base},$$

the more the refined vector $$\vec{d}^{(t)}_{CT}$$

would rely on $$\vec{d}^{(t-1)}_{base}.$$

SORT is an unsupervised tracking model, approximating each object's displacement from (t−1) to (t) with a linear constant velocity model. This is accomplished with a Kalman filter, which is commonly used for state transition prediction in linear dynamic systems. A Kalman filter is created for each tracklet, and updated by the input state of each tracked object, modeled as $O_{sort}=(p_{sort}, s_{sort})$ with the center location ($P_{sort}\in \mathbb{R}^2$) and the bounding box size ($s_{sort}\in \mathbb{R}^2$). Finally, the displacement vector from (t−1) to (t) is outputted for tracking:

$$\vec{d}^{(t-1)}_{sort} = p^{(t)}_{sort} - p^{(t-1)}_{sort} \quad (2)$$

CenterTrack outputs object displacement vectors from (t) to (t−1). Using these displacements, new detection centers are translated backwards to the previous frame. The matching cost matrix $m^{CT}\in \mathbb{R}^{(N\times M)}$ is then computed as the Euclidean distances between the centers of N tracked objects and M translated detections. For the $i^{th}$ tracked object and the $j^{th}$ translated detection:

$$m^{CT}_{ij} = \left|p^{(t-1)}_i - \left(p^{(t)}_j + \vec{d}^{(t)}_{CT_j}\right)\right| \quad (3)$$

From SORT, another forward matching cost matrix $m^{sort}\in \mathbb{R}^{(N\times M)}$ is obtained between N predicted locations of (t−1) objects frame and M new detections at (t):

$$m^{sort}_{ij} = \left\|\left(p^{(t-1)}_i + \vec{d}^{(t-1)}_{sort_j}\right) - p^{(t)}_j\right\| \quad (4)$$

All the cell detections used in CycleTrack are outputted by the CenterNet backbone of CenterTrack. To combine the matching estimates from CenterTrack and SORT, the optimal matching cost matrix for CycleTrack is first generated by selecting the smaller distance for each element in these two matching cost matrices $$m^{Cycle}_{ij} = \min\left(m^{CT}_{ij}, m^{sort}_{ij}\right).$$

Then, a greedy matching algorithm is applied to match detections to the tracked objects with the closest mutual distances based on $$m^{Cycle}_{ij}.$$

Moreover, as an additional restriction, if all the distances of a detection in the matrix are out of a reasonable range, which is defined as two times of the average diameters of cells in the current frame, it will be regarded as unmatched and a new tracklet will be created for it. The threshold is set adaptively to be the average distance between adjacent cells in the same frame.

The disclosed model was trained and evaluated on videos of human ventral tongue capillaries acquired by the OBC system. The OBC system uses a Green LED as the light source with an illumination-detection offset of around 200 μm using a 40×1.15 NA water immersion microscope objective, videos with a frame size of 1280×812 pixels were acquired at 160 Hz and 0.5 ms exposure time, with a 416×264 $\mu m^2$ field of view.

Videos from 4 different ventral tongue capillaries were acquired. During model hyperparameter tuning, 4-fold cross validation was applied by splitting the dataset based on capillaries to prevent capillary feature leakage. And with the optimal hyperparameters, the final model is trained on videos from 3 capillaries while another capillary's videos were left for test. The training dataset contains 942 fully annotated frames from 9 different sequences with a total of 4570 masks for 607 cells. Manual annotations were created by a trained expert, each of which consists of a labeled mask and a tracking ID. All tracking IDs are consistent across frames for the same cell in a sequence. The testing dataset contained a sequence with 300 annotated frames, with 901 masks for 197 cells. For further validation of cell count accuracy, CycleTrack was applied to eight additional videos with 1000 frames each. These videos had manually determined cell counts as ground truth but no mask annotations.

TABLE 1

MOT Metrics on Comparative Models.

| | Detection | | ID match | | | Trajectory | | | | Overall | Speed |
|---|---|---|---|---|---|---|---|---|---|---|---|
| Model | Prcn↑ | Rcll↑ | IDP↑ | IDR↑ | IDF1↑ | MT↑ | ML↓ | IDSw↓ | Frag↓ | MOTA↑ | (Hz) |
| Tracktor++ | 88.3 | 83.8 | 63.6 | 57.3 | 61.1 | 31.1 | 24.8 | 26.7 | 15.7 | 46.4 | 1.5 |
| MaskTrack | 90.3 | 85.8 | 67.2 | 64.52 | 65.9 | 41.2 | 22.9 | 38.1 | 24.5 | 53.2 | 2.6 |
| CN + SORT | 92.6 | 82.7 | 68.6 | 64.0 | 66.1 | 51.7 | 18.5 | 69.1 | 43.4 | 57.4 | 16.8 |
| CenterTrack | 92.6 | 82.7 | 75.5 | 74.3 | 71.6 | 65.8 | 15.6 | 59.8 | 30.6 | 62.4 | 12.0 |
| CycleTrack | 92.6 | 82.7 | 78.2 | 72.1 | 76.1 | 72.7 | 14.3 | 34.5 | 21.8 | 66.3 | 12.0 |

*CN + SORT: CenterNet-based SORT; Prcn: precision; Rcll: recall; IDP/IDR: ID precision/recall, MT/ML(%): most tracked/lost trajectory; IDSw(%): an ID switches to a different tracklet; Frag(%): fragment tracklets from miss detection.

CycleTrack builds upon the CenterNet-based CenterTrack and SORT in Pytorch, with a modified DLA model as a backbone. The training inputs were made up of frame pairs after standard normalization. To enhance the model generalization on the limited dataset, data augmentation, including rotation uniformly varying within 15 degrees, vertical/horizontal flips, and temporal flips with a probability of 0.5, were applied to simulate various blood cell flows. To simulate variation of up to 3× flow velocity, frame pairs were randomly generated within the frame range of [−3,3]. During training, the focal loss in the original CenterNet work was used for object detection and offset loss Loff for displacement vector regression, optimized with Adam with a learning rate of $10^{-4}$ and batch size of 16 for 300 epochs. The learning rate was reduced by half every 60 epochs. The CycleTrack runtime was tested on an Intel Xeon E5-2620 v4 CPU with a Titan V GPU. Detections were only tracked with a confidence ω≥0:6. Test-time detection errors simulation was also used to better tolerate the imperfect object detection by setting random false positive and false negative ratios as $\lambda_{fp}$=0:1 and $\lambda_{fn}$=0:4. For model evaluations, the CycleTrack was compared with several benchmark online MOT models including CenterNet-based SORT, CenterTrack, and appearance-based trackers such as Tracktor++ and MaskTrack.

Figure 6:
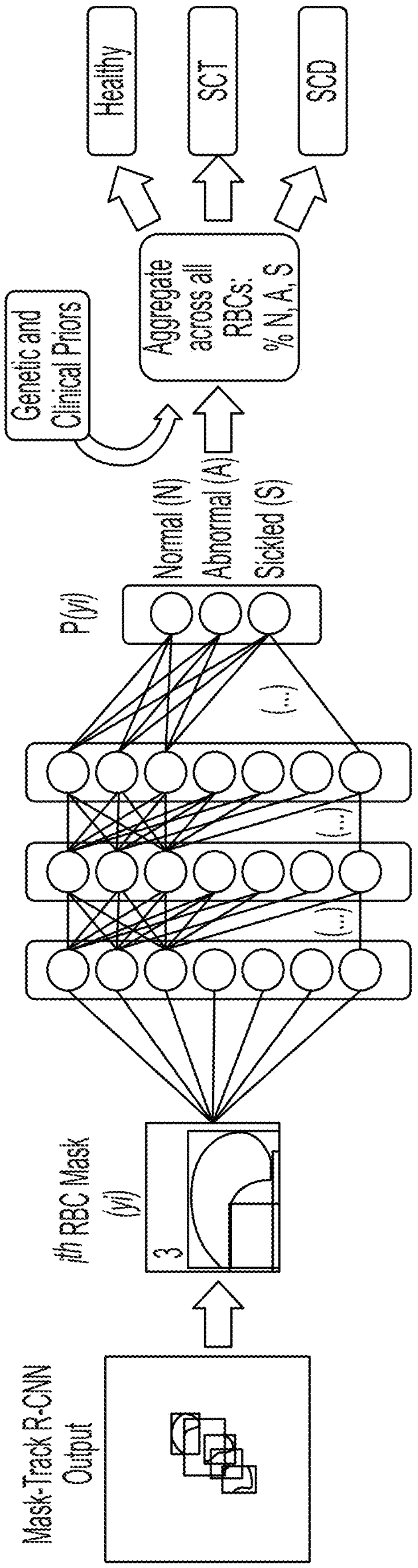
FIG. 6 shows a neural network architecture according to examples of the present disclosure.

FIG. 6 shows a neural network architecture according to examples of the present disclosure. Stochastic computing convolutional neural network (SC-CNN) 302 obtains mask-track R-CNN output 304 that is transformed into $i^{th}$ RBC mask 306.

Figure 7A:
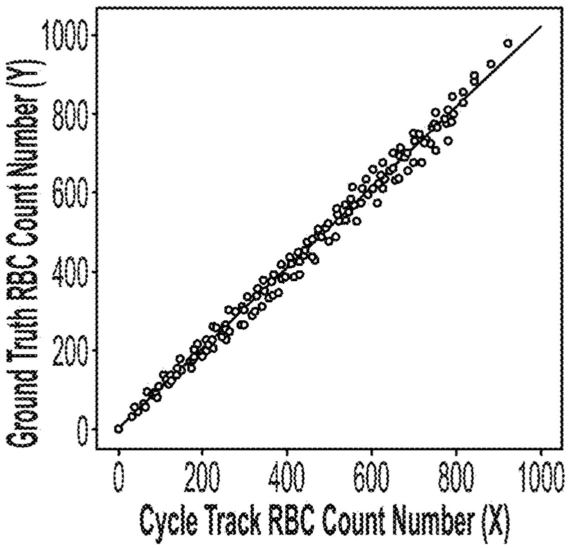
FIG. 7A shows a correlation between ground truth blood cell count and results from CycleTrack.
Figure 7B:
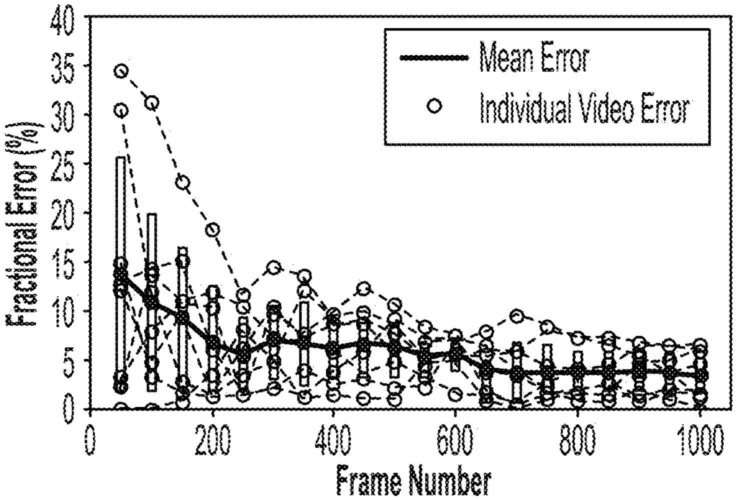
FIG. 7B shows fractional Counting Errors Across Frames.
Figure 7C:
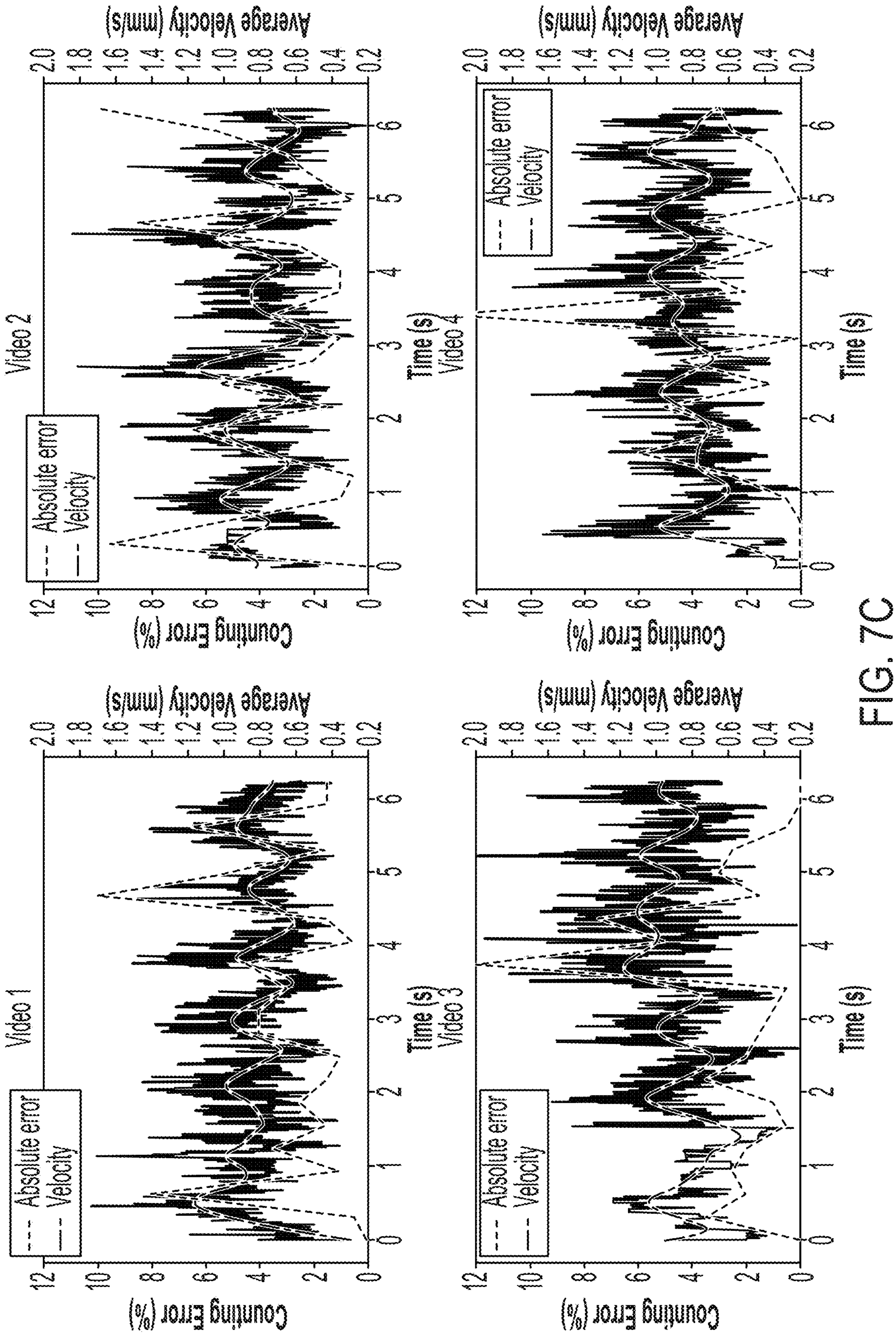
FIG. 7C shows a velocity Estimation and Absolute Counting Errors Over 4 Different Test Videos.

FIG. 7A shows a correlation between ground truth blood cell count and results from CycleTrack. FIG. 7B shows fractional Counting Errors Across Frames. Curve: individual absolute percentage counting errors; black curve is the mean, and grey bars are the standard deviations of errors over 8 test videos. FIG. 7C shows a velocity Estimation and Absolute Counting Errors Over 4 Different Test Videos. The faded lines: average velocity of all objects; the solid blue lines: a lowpass filtered average velocity; the lines: the absolute cell counting errors over the nearby 50 frames.

A quantitative analysis of performance is presented in Table 1, where the MOT metrics are listed of comparative models tested on an unseen 300-frame video with full annotations. With similar detection accuracy, it is first observed that position-based trackers have better tracking performance over appearance-based trackers in our videos. It is also important to note that CycleTrack outperforms all other trackers in the tracking metrics, especially in terms of multiple object tracking accuracy (MOTA), which provides general evaluation of both object detection and tracking, and ID F1 score (IDFI). It is also notice that, compared with local trackers without re-identification (Re-ID) models, like SORT and CenterTrack, the major improvement of our framework is in the significant reduction of ID switches. ID switches have widely shown to be a good metric that reflects stable long, consistent tracks. For local trackers only focusing on two consecutive frames, a missed detection or biased displacement vector would cause an irreparable break of tracklets that leads to high ID switches and fragments. The reduction of ID switches demonstrates that local association refinement using back-and-forth tracking paths effectively compensate for tracking errors from unidirectional trackers, thus achieving stable long-term tracking.

The cell counting accuracy on 8 1000-frame videos were also evaluated with manually counted ground truth (without masks). The agreement between CycleTrack count and ground truth is shown FIG. 7A. The correlation coefficient (γ) calculated from these experiments is 0.9960 which indicated a very strong positive relation between CycleTrack count and ground truth. FIG. 7B shows the percentage of absolute counting error change across time on these 8 videos. As frame number increases, a descending trend is observed in both average and variance of counting errors, which decrease quickly at first 300 frames and then become more stable as the base vector from CenterTrack gradually stabilizes to the right direction of capillary flow. When the frame number exceeds 600 when model typically has counted more than 400 cells, the average error stabilizes below 5%. This indicates that, to get a reliable counting in clinical scenarios, OBC videos are suggested to have at least 600 frames (3:75 s). By 1000 frames (6:25 s), the CycleTrack method reaches a state-of-the-art average counting accuracy of 96:58±2:43%, compared to 93:45% and 77:02% accuracy of original CenterTrack and SORT respectively. This demonstrates that, with the same object detector, stabler long-time tracking contributes to a great improvement to final counting accuracy. A verification study by Vis et al. reported that the state-of-the-art analytical blood cell count accuracy of routine hematology is above 96:8%. And the average coefficient of variation of fingerprick blood cell counts from point-of-care instruments was higher by at least 3 times. CycleTrack achieves a promising average accuracy of 96:58% on 1000-frame OBC videos compared with manual counting ground truths, which is close to the acceptable clinical accuracy as a point-of-care technique.

The runtime mainly depends on the input image resolution and the number of objects detected and tracked. With 16-bit image inputs, CycleTrack ran at around 12 frames per second. The runtime of comparative models is shown in the last column in Table 1. Thanks to the efficiency of CenterNet, CycleTrack has a great advantage over other trackers in terms of speed while maintaining a good detection accuracy. Moreover, as SORT is a fast, unsupervised online tracking model capable of real-time tracking incorporating this model in CycleTrack adds no significant computational costs over the original CenterTrack.

FIG. 7C shows four examples of the estimated average velocity across frames from predicted displacement vectors with the absolute errors of the past 50 frames. From these data, it is observed that a clear sinusoidal signal is present at a frequency of approximately 1 Hz. This falls within the expected normal physiological heartbeat of around 60 beats per minute. Therefore, it is believed possible to assess other significant physiological information beyond blood counts with this technology, such as blood flow metrics and vital signs. Moreover, these data show that the absolute error peaks tend to align with the peak blood flow velocity, which indicates a correlation between counting errors and flow velocity.

In summary, a deep tracking model, called CycleTrack, is disclosed that automatically counts blood cells from OBC videos. CycleTrack combines two online tracking models, SORT and CenterTrack, and predicts back-and-forth cell displacement vectors to achieve optimal matching between newly detected cells and previously tracked cells in two consecutive frames with minimal increase in runtime. Two simple assumptions were made about blood flow that enhance the accuracy of our model: (1) cells in the same capillary tend to flow in similar directions in a single frame, and (2) individual cells move with a roughly linear constant velocity across frames. CycleTrack results outperform four existing multi-object tracking models and demonstrates robust cell counting with an average accuracy of 96.58% that is close to clinical acceptance accuracy. In addition, CycleTrack is a promising model to explore other valuable clinical biomarkers from OBC videos, like blood velocity and heartrate.

Figure 8:
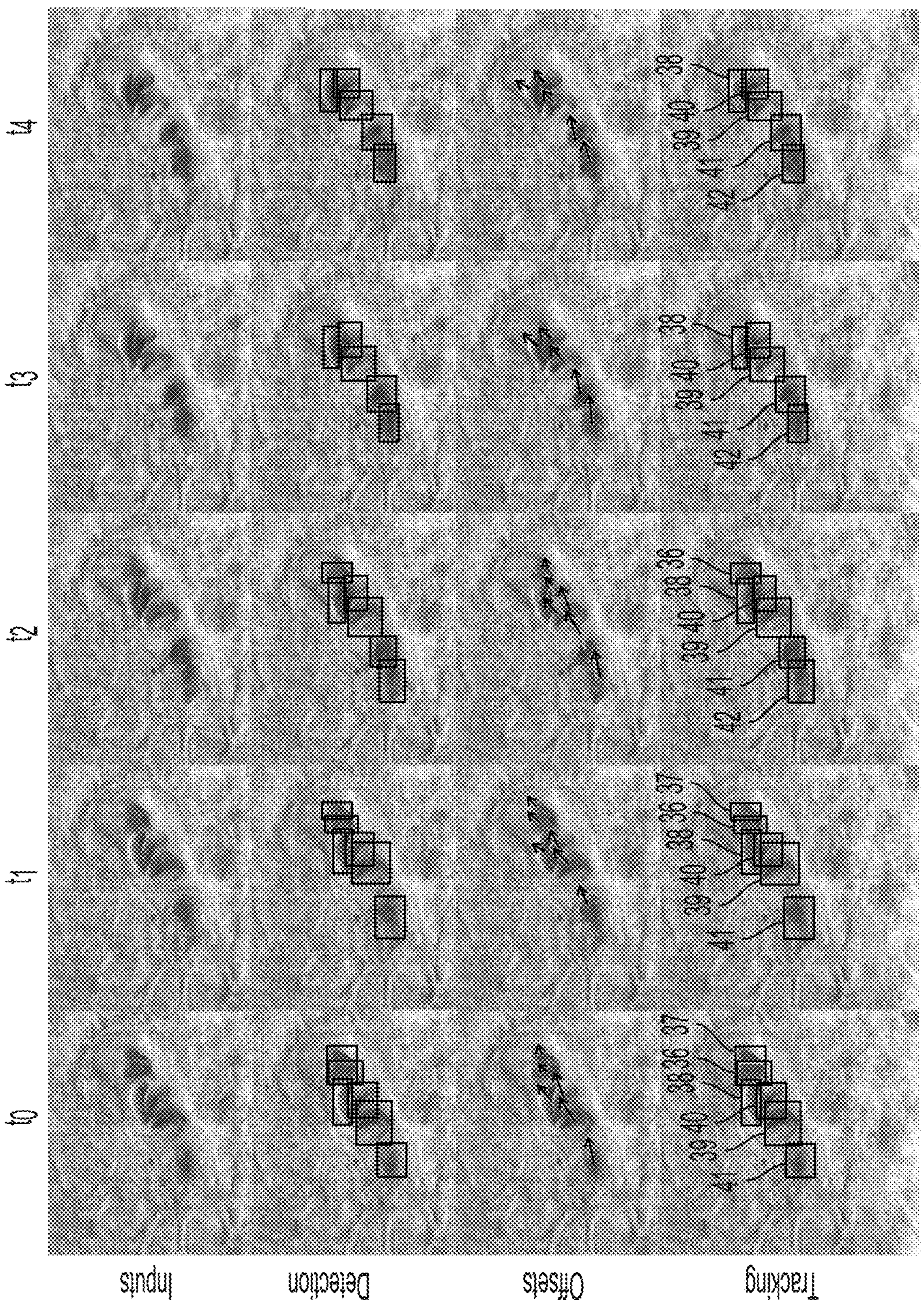
FIG. 8 shows examples of CycleTrack outputs, where the first row shows the original inputs at consecutive frames ($t_0$-$t_4$), the second row shows the bounding boxes predicted by the object detector (CenterNet) from CycleTrack, the third row shows forward displacement vectors of the optimal matching plan by CycleTrack, and the last row shows the final tracking results according to examples of the present disclosure.

FIG. 8 shows examples of CycleTrack outputs, where the first row shows the original inputs at consecutive frames ($t_0$-$t_4$), the second row shows the bounding boxes predicted by the object detector (CenterNet) from CycleTrack, the third row shows forward displacement vectors of the optimal matching plan by CycleTrack, and the last row shows the final tracking results according to examples of the present disclosure. Tracked cells in different frames would be assigned to an identical tracking ID.

Figure 9:
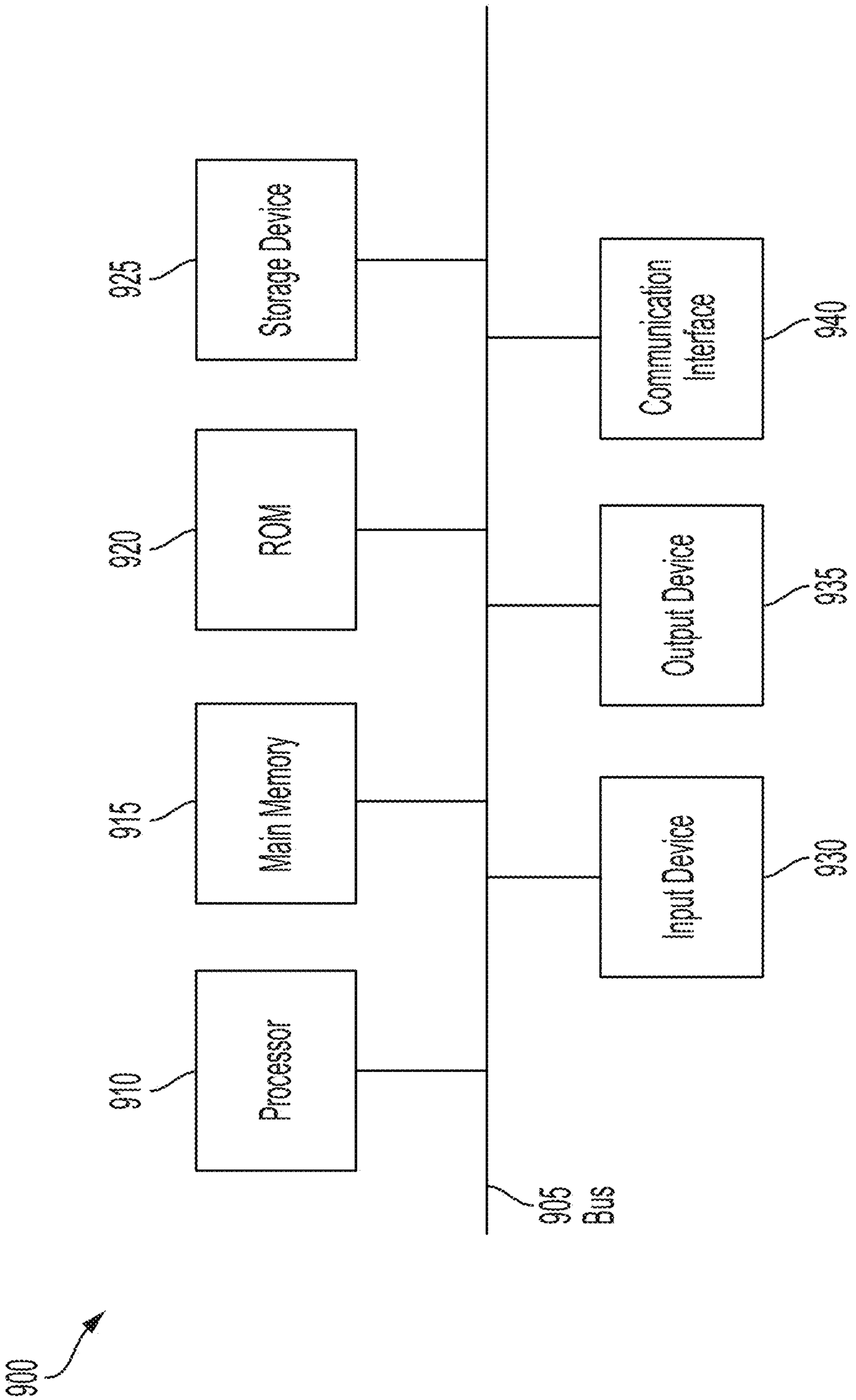
FIG. 9 illustrates example components of a device that may be used within environment of FIG. 2.

FIG. 9 illustrates example components of a device 900 that may be used within environment 200 of FIG. 2. Device 900 may correspond the image capture device 210, the blood count determination system 220, and/or the diagnostic workflow system 230. Each of the image capture device 210, the blood count determination system 220, and/or the diagnostic workflow system 230 may include one or more devices 900 and/or one or more components of device 900.

As shown in FIG. 9, device 500 may include a bus 905, a processor 910, a main memory 915, a read only memory (ROM) 920, a storage device 925, an input device 950, an output device 955, and a communication interface 940.

Bus 905 may include a path that permits communication among the components of device 900. Processor 910 may include a processor, a microprocessor, an application specific integrated circuit (ASIC), a field programmable gate array (FPGA), or another type of processor that interprets and executes instructions. Main memory 915 may include a random access memory (RAM) or another type of dynamic storage device that stores information or instructions for execution by processor 910. ROM 920 may include a ROM device or another type of static storage device that stores static information or instructions for use by processor 910. Storage device 925 may include a magnetic storage medium, such as a hard disk drive, or a removable memory, such as a flash memory.

Input device 950 may include a component that permits an operator to input information to device 900, such as a control button, a keyboard, a keypad, or another type of input device. Output device 955 may include a component that outputs information to the operator, such as a light emitting diode (LED), a display, or another type of output device. Communication interface 940 may include any transceiver-like component that enables device 500 to communicate with other devices or networks. In some implementations, communication interface 940 may include a wireless interface, a wired interface, or a combination of a wireless interface and a wired interface. In embodiments, communication interface 940 may receive computer readable program instructions from a network and may forward the computer readable program instructions for storage in a computer readable storage medium (e.g., storage device 925).

Device 900 may perform certain operations, as described in detail below. Device 900 may perform these operations in response to processor 910 executing software instructions contained in a computer-readable medium, such as main memory 915. A computer-readable medium may be defined as a non-transitory memory device and is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. A memory device may include memory space within a single physical storage device or memory space spread across multiple physical storage devices.

The software instructions may be read into main memory 915 from another computer-readable medium, such as storage device 925, or from another device via communication interface 940. The software instructions contained in main memory 915 may direct processor 910 to perform processes that will be described in greater detail herein. Alternatively, hardwired circuitry may be used in place of or in combination with software instructions to implement processes described herein. Thus, implementations described herein are not limited to any specific combination of hardware circuitry and software.

In some implementations, device 900 may include additional components, fewer components, different components, or differently arranged components than are shown in FIG. 5.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the disclosure may include a system, a method, and/or a computer program product at any possible technical detail level of integration. The computer program product may include a computer readable storage medium (or media) having computer readable program instructions thereon for causing a processor to carry out or execute aspects and/or processes of the present disclosure.

In embodiments, the computer readable program instructions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on a user's computer, partly on the user's computer, as a stand-alone software package, partly on the user's computer and partly on a remote computer or entirely on the remote computer or server.

In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

In embodiments, a service provider could offer to perform the processes described herein. In this case, the service provider can create, maintain, deploy, support, etc., the computer infrastructure that performs the process steps of the disclosure for one or more customers. These customers may be, for example, any business that uses technology. In return, the service provider can receive payment from the customer(s) under a subscription and/or fee agreement and/or the service provider can receive payment from the sale of advertising content to one or more third parties.

The foregoing description provides illustration and description, but is not intended to be exhaustive or to limit the possible implementations to the precise form disclosed. Modifications and variations are possible in light of the above disclosure or may be acquired from practice of the implementations.

It will be apparent that different examples of the description provided above may be implemented in many different forms of software, firmware, and hardware in the implementations illustrated in the figures. The actual software code or specialized control hardware used to implement these examples is not limiting of the implementations. Thus, the operation and behavior of these examples were described without reference to the specific software code—it being understood that software and control hardware can be designed to implement these examples based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

While the present disclosure has been disclosed with respect to a limited number of embodiments, those skilled in the art, having the benefit of this disclosure, will appreciate numerous modifications and variations there from. It is intended that the appended claims cover such modifications and variations as fall within the true spirit and scope of the disclosure.

No element, act, or instruction used in the present application should be construed as critical or essential unless explicitly described as such. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise.

What is claimed is:

1. A non-invasive blood analysis system comprising:

an image capture device;

a capillaroscope attachable to the image capture device, the capillaroscope comprising:

a light source configured to provide offset light at an angle and location offset from a horizontal optical axis of the capillaroscope to a target location of a patient;

a reverse lens configured to receive remitted light from the target location; and one or more telescopic lenses through which oblique illumination passes therethrough to a lens of the image capture device after passing through the reverse lens, wherein the image capture device further comprises a processor that outputs an operational blood count data as input to a diagnostic workflow to execute the diagnostic workflow based on the remitted light that passes through the lens of the image capture device to provide the non-invasive blood analysis.

2. The non-invasive blood analysis system of claim 1, wherein the image capture device is a portable device.

3. The non-invasive blood analysis system of claim 1, wherein the image capture device is a mobile phone.

4. The non-invasive blood analysis system of claim 1, wherein the image capture device is a handheld phone.

5. The non-invasive blood analysis system of claim 1, wherein the capillaroscope further comprises a beam splitter configured to direct light from the light source to provide the offset light.

6. The non-invasive blood analysis system of claim 1, wherein the light source is angled towards a patient site and circumvents the reverse lens.

7. The non-invasive blood analysis system of claim 1, wherein the capillaroscope further comprises one or more beam conditioning components to receive light from the light source or the remitted light.

8. The non-invasive blood analysis system of claim 1, wherein the diagnostic workflow is executed using a trained neural network.

9. The non-invasive blood analysis system of claim 8, wherein the trained neural network is trained using supervised, unsupervised, or semi-supervised training.

10. The non-invasive blood analysis system of claim 1, wherein the diagnostic workflow includes at least one of:

cellular volume determination to determine complete blood count;
sickle cell analysis;
blood cell concentration determination;
hematocrit determination; or
hemoglobin concentration determination.

11. The non-invasive blood analysis system of claim 1, wherein the operational blood count includes at least one of:
complete blood count (CBC) data;
blood cell masks; viscosity of blood cells;
rolling/stickiness of blood cells;
blood cell distribution width for sepsis; or
temporal trends of blood cell behavior.

12. The non-invasive blood analysis system of claim 1, further comprising a light guide that couples output light from the light source to a patient site and a relay lens system that couples reflected light from the patient site to the reverse lens.

13. The non-invasive blood analysis system of claim 1, wherein the image capture device comprises an application that produces a user interface that shows images captured by the capillaroscope, provides feedback to a user as to a best position of the capillaroscope to acquire accurate measurements, and display results produced by the diagnostic workflow.

14. The non-invasive blood analysis system of claim 1, wherein the image capture device is configured to acquire data in a burst mode to allow short windows of high-speed video to be captured.

15. The non-invasive blood analysis system of claim 1, further comprising a cap that is positioned around the outside of the reverse lens, wherein the cap is disposable or cleanable between uses.

16. The non-invasive blood analysis system of claim 15, wherein the cap provides a suction to stabilize the capillaroscope during use.

17. The non-invasive blood analysis system of claim 1, wherein the image capture device is configured to acquire images at different focal planes during use and produce three-dimensional data that is used by a diagnostic workflow for analyzing 3D cells for diagnosis.

18. A non-invasive blood analysis system comprising:
a capillaroscope attachable to an image capture device, the capillaroscope comprising:
a light source configured to provide offset light at an angle and location offset from a horizontal optical axis of the capillaroscope to a target location of a patient;
a reverse lens configured to receive remitted light from the target location;
one or more telescopic lenses through which the remitted light passes therethrough to a lens of the image capture device after passing through the reverse lens; and
a processor that outputs an operational blood count data as input to a diagnostic workflow to execute the diagnostic workflow based on the remitted light that passes through the lens of the image capture device to provide the non-invasive blood analysis.

19. A non-invasive blood analysis system comprising:
an image capture device comprising a light source;
a light guide that provides light from the light source to a patient site;
a capillaroscope attachable to the image capture device, the capillaroscope comprising:
a reverse lens through which remitted light from the patient site passes therethrough; and
one or more telescopic lenses through which oblique illumination passes therethrough to a lens of the image capture device after passing through the reverse lens,
wherein the image capture device further comprises a processor that outputs an operational blood count data as input to a diagnostic workflow to execute the diagnostic workflow based on the remitted light that passes through the lens of the image capture device to provide the non-invasive blood analysis.

* * * * *